(12) United States Patent
Rasmusse et al.

(10) Patent No.: US 9,822,146 B2
(45) Date of Patent: *Nov. 21, 2017

(54) PROCESS FOR THE MANUFACTURE OF DEGARELIX AND ITS INTERMEDIATES

(71) Applicant: Ferring B.V., Hoofddorp (NL)

(72) Inventors: Jon Holbech Rasmusse, Lyngby (DK); Jens Fornsgaard, Farum (DK); Stefan Hansen, Copenhagen V (DK); Palle Hedengran Rasmussen, Taastrup (DK); Wolfgang Oliver Wachs, Nykoebing Sjaelland (DK)

(73) Assignee: Ferring B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,218

(22) Filed: Jun. 23, 2015

(65) Prior Publication Data

US 2016/0145301 A1 May 26, 2016

Related U.S. Application Data

(63) Continuation of application No. 13/881,744, filed as application No. PCT/EP2011/068735 on Oct. 26, 2011, now Pat. No. 9,090,656.

(30) Foreign Application Priority Data

Oct. 27, 2010 (EP) .................................... 10189032

(51) Int. Cl.
| | | |
|---|---|---|
| C07K 7/06 | (2006.01) | |
| C07K 1/00 | (2006.01) | |
| C07K 7/04 | (2006.01) | |
| C07K 1/10 | (2006.01) | |
| C07K 1/08 | (2006.01) | |
| C07K 1/02 | (2006.01) | |
| A61K 38/04 | (2006.01) | |
| A61K 38/08 | (2006.01) | |
| C07K 5/083 | (2006.01) | |
| C07K 5/087 | (2006.01) | |
| C07K 5/09 | (2006.01) | |
| C07K 7/23 | (2006.01) | |

(52) U.S. Cl.
CPC .............. *C07K 7/06* (2013.01); *A61K 38/04* (2013.01); *A61K 38/08* (2013.01); *C07K 1/00* (2013.01); *C07K 1/02* (2013.01); *C07K 1/023* (2013.01); *C07K 1/026* (2013.01); *C07K 1/08* (2013.01); *C07K 1/10* (2013.01); *C07K 5/081* (2013.01); *C07K 5/0812* (2013.01); *C07K 5/0815* (2013.01); *C07K 7/04* (2013.01); *C07K 7/23* (2013.01); *Y02P 20/55* (2015.11)

(58) Field of Classification Search
None
See application file for complete search history.

(56) References Cited

U.S. PATENT DOCUMENTS

| | | |
|---|---|---|
| 3,773,919 A | 11/1973 | Boswell |
| 5,506,207 A | 4/1996 | Rivier et al. |
| 5,516,887 A | 5/1996 | Deghenghi |
| 5,595,760 A | 1/1997 | Cherif-Cheikh |
| 5,821,230 A | 10/1998 | Jiang et al. |
| 5,860,957 A | 1/1999 | Jacobsen et al. |
| 5,863,549 A | 1/1999 | Tarantino |
| 5,925,730 A | 7/1999 | Semple et al. |
| 6,214,798 B1 | 4/2001 | Semple et al. |
| 6,503,534 B1 | 1/2003 | Pellet et al. |
| 6,875,843 B2 | 4/2005 | Jacobson |
| 2004/0038903 A1 | 2/2004 | Luck et al. |
| 2004/0138610 A1 | 7/2004 | Cormier et al. |
| 2005/0245455 A1 | 11/2005 | Luck et al. |
| 2006/0135405 A1 | 6/2006 | Rischer et al. |
| 2008/0032935 A1 | 2/2008 | Engel et al. |
| 2009/0018085 A1 | 1/2009 | Luck et al. |

(Continued)

FOREIGN PATENT DOCUMENTS

| | | |
|---|---|---|
| CN | 1411803 A | 4/2003 |
| EP | 0 002 749 B1 | 10/1983 |

(Continued)

OTHER PUBLICATIONS

"Alkaline Phosphatase" GP Notebook (Sep. 12, 2011), http://gpnotebook.co.uk/simplepage.cfm?ID=-1932525548.
Agerso, et al., "The dosing solution influence on the pharmacokinetic of degarelix, a new GnRH antagonist, after s.c. administration to beagle dogs," European Journal of Pharmaceutical Sciences, vol. 20, pp. 335-340, 2003.
Albertsen et al., Reduced Risk of Cardiovascular (CV) Events and Death in Patients (PTS) Receiving Degarelix Compared with LHRH agonists (2012).
Albertsen, et al. "Cardiovascular Morbidity Associated with Gonadotropin Releasing Hormone Agonist and an Antagonist," European Urology (2013), https://dx.doi.org/10.16/j.eururo.2013.10,032.
Andersson et al., "Large-Scale Synthesis of Peptides," Biopolymers (Peptide Science), pp. 227-250, 2000.

(Continued)

*Primary Examiner* — Marcela M Cordero Garcia
*Assistant Examiner* — Catherine Mader
(74) *Attorney, Agent, or Firm* — Finnegan, Henderson, Farabow, Garrett & Dunner LLP

(57) ABSTRACT

The present invention relates to a liquid (or solution)-phase manufacturing process for preparing the decapeptide Degarelix, its protected precursor, and other useful intermediates. The invention further relates to polypeptides useful in the solution-phase manufacturing process and to the purification of Degarelix itself. Degarelix can be obtained by subjecting a Degarelix precursor according to formula II: $(P_1)AA_1-AA_2-AA_3-AA_4(P_4)-AA_5-AA_6(P_6)-AA_7-AA_8(P_8)-AA_9-AA_{10}-NH_2$ (II) or a salt or solvate thereof, to a treatment with a cleaving agent in an organic solvent, wherein $P_1$ is an amino protecting groups; preferably acetyl; $P_4$ is hydrogen or a hydroxyl protecting group, preferably a hydroxyl protecting group; $P_6$ is hydrogen or an amino protecting groups; preferably an amino protecting groups; and $P_8$ is an amino protecting group.

5 Claims, 12 Drawing Sheets

(56) References Cited

U.S. PATENT DOCUMENTS

Figure 2:
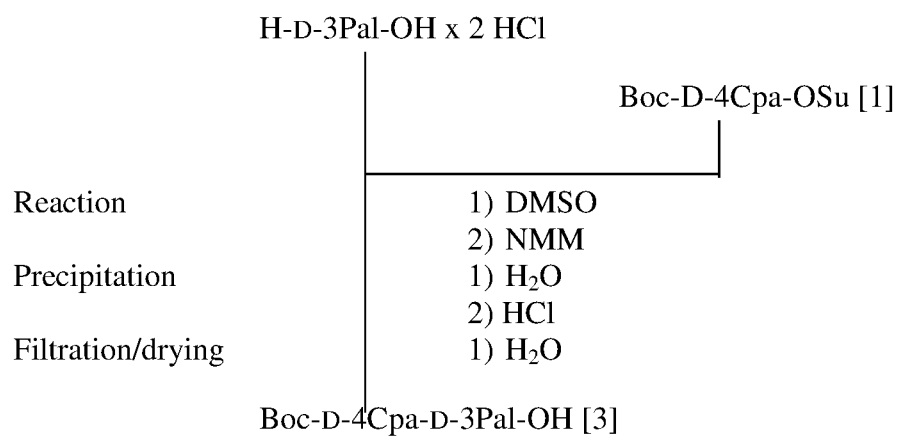

| | | |
|---|---|---|
| 2009/0203622 A1 | 8/2009 | Persson |
| 2009/0209939 A1 | 8/2009 | Verespej et al. |
| 2010/0286603 A1 | 11/2010 | Winderstrom |
| 2010/0305042 A1 | 12/2010 | Olesen et al. |
| 2011/0039787 A1 | 2/2011 | Petri et al. |
| 2011/0053846 A1 | 3/2011 | Luck et al. |
| 2012/0172302 A1 | 7/2012 | Petri et al. |
| 2013/0018223 A1 | 1/2013 | Joseph |
| 2013/0029910 A1 | 1/2013 | Meulen et al. |
| 2013/0281661 A1 | 10/2013 | Rasmusse et al. |
| 2013/0281662 A1 | 10/2013 | Kalita et al. |
| 2013/0295166 A1 | 11/2013 | Grenier et al. |

FOREIGN PATENT DOCUMENTS

| | | |
|---|---|---|
| EP | 0 556 034 A1 | 8/1993 |
| EP | 1 003 774 B1 | 5/2000 |
| EP | 1630169 | 8/2007 |
| EP | 1 967 202 A1 | 9/2008 |
| FR | 2 776 520 A | 10/1999 |
| WO | WO 97/34923 | 9/1997 |
| WO | WO 98/46634 | 10/1998 |
| WO | WO 99/26964 A1 | 6/1999 |
| WO | WO 03/006049 A1 | 10/2003 |
| WO | WO 2007/130809 A2 | 11/2007 |
| WO | WO 2008/135989 A1 | 3/2008 |
| WO | WO 2009/101533 A1 | 8/2009 |
| WO | WO 2011/004260 A2 | 1/2011 |

OTHER PUBLICATIONS

Austria_Codex Fachinformation 2006/2007.
Behn, et al., "The obesity epidemic and its cardiovascular consequences," (2006) Curr. Opin. Cardiol. vol. 21, pp. 353-360.
Berges, et al., "Effect of a new leuprorelin formulation on testosterone levels in patients with advanced prostate cancer," (2006), Cur. Med. Res. Opin., vol. 22, No. 4, pp. 649-655.
Boccon-Gibod et al: "Optimising Hormone Therapy in Advanced Disease" European Urology Supllements, vol. 4, No. 8, Nov. 1, 2005 (Nov. 1, 2005), pp. 21-29, XP005112815 ISSN: 1569-9056.
Boccon-Gibod, et al., "Cyproterone Acetate Lead-In Prevents Initial Rise of Serum Testosterone Induced by Luteinizing Hormone-Releasing Hormone Analogs in the Treatment of Mestastatic Carcinoma of the Prostate," (1986) Euro. Urol., vol. 12, pp. 400-402.
'Bone Specific Alkaline Phosphatase,' The University of Iowa (UIHC), Department of Pathology, Laboratory Services Handbook (Sep. 11, 2011), http://www.healthcare.uiowa.edu/path_handbook/handbook/test2238.html.
Boyle et al: "Treatment of hormone sensitive prostate cancer" European Journal of Cancer. Supplement, Pergamon, Oxford, GB, vol. 3, No. 3, Oct. 1, 2005 (Oct. 1, 2005), pp. 331-338, XP005130027 ISSN: 1359-6349.
Bray, "Large-Scale manufacture of peptide therapeutics by chemical synthesis," Nature Review, vol. 2, pp. 587-593, Jul. 2003.
Broqua et al., "Effects of the New GNRH Antagonist FE200486 one the Growth of the Adrogen-Dependent Prostate Tumor Dunning R-3327H, 6th International Symposium on GnRH Analogues in Cancer and Human Reproduction," Geneva, Switzerland,Feb. 8, 2001.
Broqua, et al., "Pharmacological Profile of a New, Potent, and Long-Acting Gonadotropin-Releasing Hormone Antagonist: Degarelix," The Journal of Pharmacology and Experimental Therapeutics, vol. 301, pp. 95-102, 2002.
Cancer Trends Progress Report, http://progressreport.cancer.gov.
Cetrotide TM package insert (Aug. 11, 2000).
Chernecky, and Berger, "Laboratory Tests and Diagnostic Procedures," (2008) Fifth Edition, WB Saunders & Company, Philadelphia. ISBN-978-1-14160-3704-0.
Council of Europe, Strasbourg, "European Pharmacopoeia 6263" European Directorate for the Quality of Meicines & Healthcare (2007).

Council of Europe, Strasbourg, "European Pharmacopoiea6748" European Directorate for the Quality of Meicines & Healthcare (2007).
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
Crawford et al., "Long term tolerability and efficacy of degarelix: 5-year results from a phase III extension trial with a one-arm crossover from leuprolide to degarelix", Urologic Oncology, School of Medicine, University of Colorado Denver, pp. 1-18; Mar. 22, 2014.
Crawford et al., Degarelix Versus LHRH Agonists: Differential Skeletall Morbidity Outcomes from a Pooled Analysis of Six Comparative Randomised Clinical Trials (2012).
de la Rosette et al., "Efficacy and safety of androgen deprivation therapy after switching from monthly leuprolide to monthly degarelix in patients with prostate cancer," 65(5) International Journal of Clinical Practice 559-66 (2011).
de Pinieux, et al., "Clinical and Experimental Progression of a New Model of Human Prostate Cancer and Therapeutic Approach," American Journal of Pathology, vol. 159, No. 2, Aug. 2001, 753-764.
Debruyne Franse M J: "Gonadotropin-releasing hormone antagonist in the management of prostate cancer." Reviews in Urology 2004, vol. 6 Suppl 7, 2004, pp. S25-S32, XP002527257 ISSN: 1523-6161.
Debruyne, et al,, "Abarelix for injectable suspension: first-in-class gonadotropin-releasing hormone antagonist for prostate cancer," (2006) Future Oncol., vol. 2, pp. 677-696.
Degarelix Study Group Tammela et al: "904Degarelix—a phase 11 multicenter, randomized dose-escalating study testing a novel gnrh receptor blocker in prostate cancer patients" Euorpean Urology Supplements, vol. 4, No. 3, Mar. 1, 2005 (Mar. 1, 2005) p. 228, XP005007365 ISSN: 1569-9056.
Demers et al., "Biochemical Markers and Skeletal Metastases," Cancer, vol. 88, pp. 2919-2926, Mar. 2, 2000.
Denis, et al., "Overview of Phase III Trials on Combined Androgen Treatment in Patients with Metastatic Prostate Cancer," (1993) Cancer, vol. 72, pp. 3888-3895.
Doehn Christian et al: "Drug evaluation: Degarelix—a potential new therapy for prostate cancer." IDrugs: The Investigational Drugs Jounral Aug. 2006, vol. 9, No. 8, Aug. 2006 (Aug. 2006), pp. 565-572, XP009105353 ISSN: 1369-7056.
Eastman et al., "Serum Alkaline Phosphatase: Normal Values by Sex and Age," 23(9) Clinical Chemistry 1769-1770 (1977).
Etzioni, et al., "Cancer Surveillance Series: Interpreting Trends in Prostate Cancer—Part III: Quantifying the Link Between Population Prostate-Specific Antigen Testing and Recent Declines in Prostate Cancer Mortality," (1999) J. Natl. Canc. Inst., vol. 91, pp. 1033-1039.
European Patent Office Communication pursuant to Article 94(3) EPC dated Apr. 10, 2014, in corresponding Application No. 11 776 745.9 (5 pages).
European Seach Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm. (Feb. 2004).
fda.gov, Label for Degarelix for injection (Dec. 24, 2008), available at www.accessdata.fda.gov/drugsatfda_docs/label/2008/022201lbl.pdf, last visited Jun. 4, 2013.
Ferlay,et al., "Estimates of the cancer incidence and mortality in Europe in 2006," Annals of Oncology, vol. 18, pp. 581-592 (2007).
Fleming,et al., "Post-therapy changes in PSA as an outcome measure in prostate cancer clinical Trials," (2006) Nature Clinical Practice Oncology, vol. 3, No. 12, pp. 658-667.
Forbes, et al., "FDA's Adverse Drug Reaction Drug Dictionary and Its Role in Post-Marketing Surveillance," (1986) Drug Inf. J., vol. 20, pp. 135-145.
Frampton et al., "Degarelix", ADIS International, Drugs, 69 (14): 1967-1976 (2009).
Garnero, "Markers of bone turnover in prostate cancer," Cancer Treatment Reviews, pp. 187-192: 27: 2001.

(56) References Cited

OTHER PUBLICATIONS

Garnick M et al: "217 Increase in the electrocardiographic QTC interval in men with prostate cancer undergoing androgen deprivation therapy: Results of three randomized controlled clinical studies", European Urology Supplements, vol. 3, No. 2, Feb. 1, 2004 (Feb. 1, 2004), p. 57, XP027186629, ISSN: 1569-9056.
Gerlinger, et al.,"Recommendation for Confidence interval and sample size calculations for the Pearl Index," (2003) The European Journal of Contraception and Reproductive Health Care, vol. 8, pp. 87-92.
Gillum, T., "The Merck Regulatory Dictionary: A Pragmatically Develop Drug Effects Vocabulary," (1989) Drug Info. J., vol. 23, pp. 217-220.
Gittelman et al., "A 1-Year, Open Label, Randomized Phase II Doe Finding Study of Degarelix for the Treatment of Prostate Cancer in North America," The Journal of Urology, vol. 80, pp. 1986-1992, Nov. 2008.
Gittelman et al: "MP-08.21: A multicentre, randomised one year dose-finding study of degarelix, a gonadotrophin-releasing hormone (GnRH) receptor blocker in prostate caner patients" Urology, Belle Mead, NJ, US vol. 70 No. 3, Sep. 1, 2007 (Sep. 1, 2007)pp. 83-84, XP022248654 ISSN:0090-4295.
Gonzalez-Barcena D et al: "Luteinzing hormone-releasing hormone hormone antagonist centrorelix as primary single therapy in patients with advanced prostatic cancer and paraplegia due to metastatic invasion of spinal cord."Urology Feb. 1995, vol. 45, No. 2, Feb. 1995 (Feb. 1995), pp. 275-281, XP02527258 ISSN: 0090-4295.
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., (1998), 159:2030-34.
Hackman, et al., "Emerging Risk Factors for Atheroslerotic Vascular Disease," (2003), JAMA, vol. 290, pp. 932-940.
Hegele et al., "Biochemical Markers of Bone Turnover in Patients with Localized and Metastasized Prostate Cancer," Journal Compilation, vol. 99, pp. 330-334, Sep. 7, 2006.
Hellerstedt, et al., "The Current State of Hormonal Therapy for Prostate Cancer," CA A Cancer Journal for Clinicians, vol. 52, pp. 154-179. (2002).
Hendrik et at, "Degarelix: A Novel Gonadotroin-Releasing Hormone (GnRH) Receptor Blocker—Results form a 1-yr, Multicentre, Randomised, Phase 2 Dosage-Finding Study in the Treatment of Prostate Cancer," European Urology 54, pp. 805-815. 2008.
Huirne J A et al: "Gonadotropin-releasing-hormone-receptor antagonists" Lancet The, Lancet Limited. London, GB, vol. 358, No. 9295, Nov. 24, 2001 (Nov. 24, 201), pp. 1793-1803, XP048g05574 ISSN: 0140-6736.
International Search Report dated Sep. 12, 2002, in Application No. PCT/GB02/03116.
Isidro-Llobet et al., "Amino Acid-Protecting Groups," Chem. Rev, pp. 2455-2504, 2009.
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologiest, May 22, 2013, 2 pages.
Iversen et al: "MP-08.18" Urology, Belle Mead, NJ, US, vol. 68, Nov. 1, 2006 (Nov. 1, 2006), p. 102, XP05709326 ISSN 0090-4295.
Jiang et al., "Betidamino Acid-Scan of the GNRH Antagonist Acyline," Journal of Medicinal Chemistry, American Chemical Socitey, Washington, US, vol. 40, 1997, pp. 3739-3748.
Jiang, et al.,"GnRH Antagonists: A New Generation of Long Acting Analogues Incorporating p-Ureido-phenylalanies at Positions 5 and 6," (2001) J. Med. Chem., vol. 44, pp. 453-467.
Keating Nancy L et al: "Diabetes and cardiovascular disease during androgen deprivation therapy for prostate cancer," Journal of Clinical Oncology: Official Journal of the American Society of Clinical Oncology Sep. 20, 2006, vol. 24, No. 27, Sep. 20, 2006 (Sep. 20, 2006), pp. 4448-4456, XP002687918, ISSN: 1527-7755.
Kirk et al., "Immediate Versus deferred treatment for advanced prostatic cancer; initial results of the Medical Research Counsel trial.," British Journal of Urology, (1997) vol. 79, pp. 235-246.
Lehmann, "Testing Statistical Hypotheses," (1986) Second Edition, John Wiley & Sons, New York, ISBN 0-471-84083-1.
Lilja, et al., "Prostate-specific antigen and prostate cancer: prediction, detection and monitoring," (2008) Nature Reviews/Cancer, vol. 8, pp. 268-278.
Lukka, et al., "Maximal androgen blockade for the treatment of metastatic prostate cancer—a systematic review," Current Oncology, vol. 13, No. 3, pp. 81-93. (2006).
Lyseng-Williamson, Katherine A., "Degarelix: a guide to its use in advanced prostate cancer," 28(5) Drugs Ther. Perspect. 6-10 (2012).
Malkin, "Are techniques used for intramuscular injection based on research evidence?" nursingtimes.net, Nursing Times; 104; 50/51, 48-51 Dec. 16, 2008.
McNeil, et al., "On the Elicitation of Preferences for Alternative Therapies," (1982) N. Engl. J. Med., vol. 306, No. 21, pp. 1259-1262.
MedDRA website, http://www.meddramsso.com. (2009).
Messing, et al., "Immediate Hormonal Therapy Compared with Observation after Radical Prostatectomy and Pelvic Lyphadenectomy in Men with Node-Positive Prostate Cancer," (1999), N. Eng. J. Med., vol. 341, pp. 1781-1788.
Miller et al., "Disease control-related outcomes from an analysis of six comparative randomised clinical trials of degarelix versus luteinising hormone-releasing hormone (LHRH) agonists," (2012).
Mongiat-Artus P et al: "Role of Luteinising Hormone Releasing Hormone (LHRH) Agonists and Hormonal Treatment in the Management of Prostate Cancer" European Urology Supplements, vol. 4, No. 5, Jul. 1, 205 (Jul. 1, 2005), pp. 4-13, XP004926296 ISSN: 1569-9056.
Mongiat-Artus, et al., "Abarelix: the first gonadotrophin-releasing hormone antagonist for the treatment of prostate cancer," (2004), Expert Opin. Pharmacother, vol. 5, pp. 2171-2179.
Montalbetti et al., "Amide bond formation and peptide coupling," Science Direct (Tetrahedron 2005), pp. 10827-10852.
National Cholesterol Education Program (NCEP) Guidelines for Interpretation of Lipid Values, XP-02729834.
NCEP ATP III Classification of Total Cholesterol, LDL-C, and HDL-C, XP-02729835.
Notice of Third Party Opposition, dated Jan. 23, 2015, in EP 2249859.
Office Action (final) dated Jan. 9, 2014, U.S. Appl. No. 12/829,467.
Office Action (final) dated Mar. 5, 2014, U.S. Appl. No. 12/155,897.
Office Action (final) dated Mar. 6, 2014, U.S. Appl. No. 12/901,270.
Office Action (final) dated Oct. 8, 2013, U.S. Appl. No. 13/381,762.
Office Action (Final) dated May 20, 2014, in co-pending U.S. Appl. No. 13/458,330.
Office Action (non-final) dated Jun. 5, 2015, U.S. Appl. No. 12/155,897.
Office Action (non-final) dated Jun. 4, 2015, U.S. Appl. No. 14/139,922.
Office Action (non-final) dated Jun. 5, 2015, U.S. Appl. No, 12/901,270.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 6, 2013, U.S. Appl. No. 12/774,113.
Office Action dated May 5, 2015, U.S. Appl. No. 13/881,751.
Office Action dated Sep. 11, 2013, in U.S. Appl. No. 12/771,199.
Office Action dated Sep. 3, 2013, in U.S. Appl. No. 13/458,330.
Office Action dated Apr. 2, 2012, in copending U.S. Appl. No. 12/368,935.
Office Action dated Aug. 27, 2014 in U.S. Appl. No. 13/881,744.
Office Action dated Dec. 3, 2013, in copending U.S. Appl. No. 12/368,713.
Office Action dated Jan. 31, 2013, in copending U.S. Appl. No. 12/901,270.
Office Action dated Mar. 1, 2011, in copending U.S. Appl. No. 12/368,713.
Office Action dated Mar. 8, 2011, in copending U.S. Appl. No. 12/155,897.

(56) References Cited

OTHER PUBLICATIONS

Office Action dated Oct. 12, 2011, in U.S. Appl. No. 12/155,897.
Office Action dated Oct. 2, 2014, in copending U.S. Appl. No. 12/829,467.
Office Action dated Oct. 22, 2009, in co-pending U.S. Appl. No. 12/155,897.
People's Republic of China First Office Action dated Feb. 25, 2013 in corresponding Application No. 201080019696.2, 2 pages.
Persad, "Leuprorelin Acetate in Prostate Cancer: A European Update," (2002) Int. J. Clin. Pract., vol. 56, No. 5, pp. 389-396.
Ramaswamy et al., "Serum Levels of Bone Alkaline Posphatase in Breast and Prostate Cancers with Bone Metastasis," Indian Journal of Clinical Biochemistry, pp. 110-113, 15(2), 2000.
Romero-Corral, et al., "Association of bodyweight with total mortality and with cardiovascular events in coronary artery disease: a systematic review of cohort studies," (2006) Lancet, 368:666-678.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) Drug Info. J., vol. 19, pp. 35-41.
Samant et al., "Novel analogues of degarelix incorporating hydroxy-, methoxy- and pegylated-urea moieties at portions 3, 5, 6 and the N-terminus," J. Med Chem. 49(12), pp. 3536-3543, 2006.
Seer Program and the National Center for Health Statistics, <http://seer.cancer.gov/.>.
Smith et al., "Cardiovascular Safety of Degarelix: Results From a 12-Month, Comparative, Randomized, Open Label, Parallel Group Phase III Trial in Patients With Prostate Cancer," 184 The Journal of Urology 2313-2319 (2010).
Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Spilker, Bert, "Guide to Cinical Trials," (1991) Raven Press, Ltd., New York, ISBN 0-88167-767-1.
Spilker, Bert, "Quality of Life and Pharmacoeconomics in Clinical Trials," (1996) Lippincott-Raven Publishers, New York, ISBN 0-7817-0332-8.
Steinberg, et al., "Degarelix: A Gonadotropin-Releasing Hormone Antagonist for the Management of Prostate Cancer," Clinical Therapeutics, vol. 31, pp. 2312-2331, 2009.
Stephens, M.D.B., "The Detection of New Adverse Drug Reactions," (1988) Stockton Press, New York, ISBN 0-333-45417-0.
Teal, et al., "Adverse Drug Experience Management: A Brief Review of the McNeil Pharmaceutical System," (1985) Drug Info. J., vol. 19, pp. 17-25.
The K-Zone, Biophysical data tables: standard man, Jul. 2004: printed Mar. 14, 2009 from www.kevinboone.com/biodat_stdman.html; 1 page.
Thompson, et al., "Sudden Death to Disease Flare With Luteinizing Hormone-Releasing Hormone Agonist Therapy for Carcinoma of the Prostate," J. Urol., (1990) vol. 144, pp. 1479-1480.
Tsai Henry K et al: Androgen deprivation therapy for localized prostate cancer and the risk of cardiovascular mortality., Journal of the National Cancer Institute Oct. 17, 2007 LNKD—PUBMED:17925537, vol. 99, No. 20, Oct. 17, 2007 (Oct. 17, 2007), pp. 1516-1524, XP002687919, ISSN: 1460-2105.
Turner, et al., "The Processing of Adverse Reactoin Reports at FDA," (1986) Drug. Inf. J., vol. 20, pp. 147-150.
van Kerrebroeck et al., "Desmopressin in the Treatment of Nocturia: A Double-Bind, Placebo-Controlled Study", European Urology, 52, (Jan. 16, 2007).
Van Poppel et al., "A One-Year, Multicentre, Randomised Study of Degarelix a Gonadatrophin-Releasing Hormone (GHRH) Receptor Blocker, in Prostate Cancer Patients," Eur Urol Supppl 2005:5(2):251.
Van Poppel et al,, "Degarelix: A Novel Gonadotropin-Releasing Hormone (GnRH) Receptor Blocker—Results from a 1-yr, Multicentre, Randomised, Phase 2 Dosage-Finding Study in the Treatment of Prostate Cancer", European Urology No. 54, pp. 805-815 (2008).
Van Poppel H et al; "23 Long-Term Evaluation of Degarelix, A Gonadotrophin-Releasing Hormone (GHRH) Receptor Blocker, Investigated in a Multicentre Randomised Study in Prostate Cancer (CAP) Patients" European Urology Supplements, vol. 6, No. 2, Mar. 1, 2007 (Mar. 1, 2007), p. 28, XP022686644 ISSN: 1569-9056 [retrieved on Mar. 1, 2007].
Van Poppel, "Evaluation of degarelix in the management of prostate cancer," Cancer Management and Research, vol. 2, pp. 39-52, 2010.
Wiegel et al., "Neoadjuvant Androgen Deprivation Therapy for Prostate Volume Reduction, Lower Urinary Tract Symptom Relief and Quality of Life Improvement in Men with Intermediate- to High-risk Prostate Cancer: A Randomised Non-inferiority Trial of Degarelix versus Goserelin plus Bicalutamide", 2 pages.
Wilson, et al,, "Leuprolide acetate: a drug of diverse clinical applications," Expert Opin. Investig. Drugs, (2007), vol. 16, pp. 1851-1863.
Wilson, et al., "Prediction of Coronary Heart Disease Using Risk Factor Categories," (1998) Circulation, 97:1837-47.
Yannucci, et al., "The Effect of Androgen Deprivation Therapy on Fasting Serum Lipid and Glucose Parameters," (2006) J. Urol., vol. 176, pp. 520-525.
Office Action (final) dated Jul. 14, 2016, U.S. Appl. No. 14/454,825.
Office Action (final) dated Mar. 10, 2016, U.S. Appl. No. 14/139,922.
Office Action (final) dated Mar. 24, 2016, U.S. Appl. No. 13/458,330.
Office Action (final) dated Apr. 8, 2016, U.S. Appl. No. 14/403,775.
Office Action (non-final) dated Feb. 19, 2016, U.S. Appl. No. 14/454,825.

Figure 1
Step 1 (Reaction step)
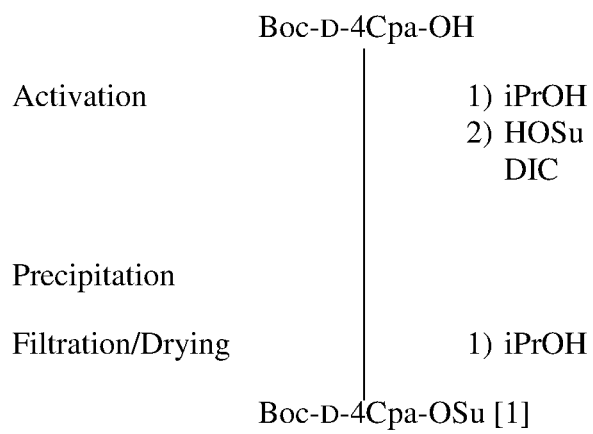
Step 2 (Reaction step)
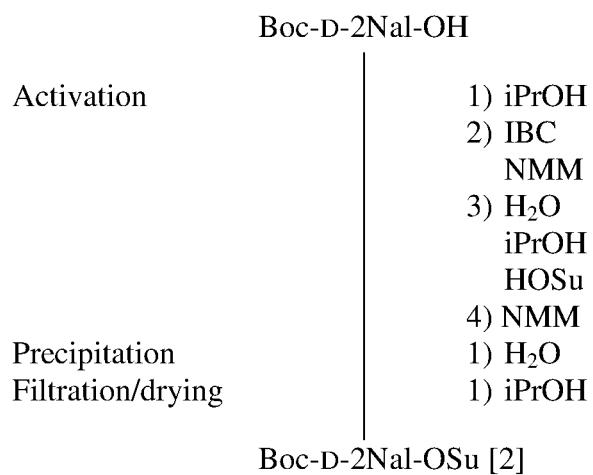

Step 3 (Reaction step)

Step 4 (Reaction step)

Step 5 (Reaction step)

Step 6 (Reaction step)

Figure 6

Step 7 (Reaction step)

Boc-4Aph(L-Hor)-D-4Aph(tBuCbm)-Leu-OBzl [12]

| | |
|---|---|
| Deprotection | 1) MSA<br>   AcOEt<br>2) 2-BuOH |
| Neutralisation | 1) TEA |
| Hydrogenation | 1) Pd/C<br>   2-BuOH<br>   $H_2$ |
| Filtration | 1) 2-BuOH |

H-4Aph(L-Hor)-D-4Aph(tBuCbm)-Leu-OH [13]

Z-Ser(tBu)-OH

| | |
|---|---|
| Dissolution | 1) MeCN |
| Activation | 1) HONp<br>2) DCC |
| Filtration | 1) MeCN |

Z-Ser(tBu)-ONp [14]

| | |
|---|---|
| Reaction | 1) NMM<br>2) DMF |
| Extraction | 1) $H_2O$/NaCl acidic<br>2) $H_2O$ acidic<br>3) $H_2O$/NaHCO$_3$<br>4) $H_2O$/NaCl acidic<br>5) $H_2O$/NaCl |
| Concentration | 1) DCHA<br>2) iPrOH |
| Precipitation | 1) AcOEt/iPrOH |
| Filtration/Drying | 1) AcOEt |

Z-Ser(tBu)-4Aph(L-Hor)-D-4Aph(tBuCbm)-Leu-OH x DCHA [15]

Step 8 (Reaction step)

Step 9 (Reaction step)

Figure 9

Z-Lys(iPr,Boc)-Pro-D-Ala-NH₂ [20]

| | |
|---|---|
| Dissolution | 1) EtOH |
| | H₂O |
| | 2) Pd/C |
| pH adjustment | 1) dil. HCl |
| Hydrogenation | 1) H₂ |
| Filtration/neutralisation | 1) dil. NaOH |
| Concentration | |
| Extraction | 1) n-BuOH |
| pH adjustment | 1) NaOH |
| Concentration | 1) AcOBu |
| Precipitation | 1) Heptane |
| Filtration/drying | 1) Heptane |

H-Lys(iPr,Boc)-Pro-D-Ala-NH₂ [21]

Figure 10

Step 10 (Reaction step)

| | Z(4-7)OH x DCHA [15] |
|---|---|
| Dissolution | 1) DMF |
| | 2) HOBt |
| |     AcOEt |
| |         H-Lys(iPr,Boc)-Pro-D-Ala-NH$_2$ [21] |
| Reaction | 1) MSA |
| | 2) DCC/AcOEt |
| Filtration | 1) AcOEt/H$_2$O |
| pH-adjustment | 1) H$_2$O/ NaHCO$_3$ |
| Extraction | 1) H$_2$O alkaline |
| | 2) H$_2$O acidic |
| | 3) H$_2$O |
| Concentration | 1) EtOH |
| | 2) AcOEt |
| Precipitation | 1) EtOH |
| |     AcOEt |
| | 2) AcOBu |
| | 3) Heptane |
| Filtration/Drying | 1) Heptane |

Z-Ser(tBu)-4Aph(L-Hor)-D-4Aph(tBuCbm)-Leu-Lys(iPr,Boc)-Pro-D-Ala-NH$_2$ [22]

Figure 11

Step 11 (Reaction step)

Z(4-10)NH$_2$ [22]

| | |
|---|---|
| Suspension | 1) EtOH/H$_2$O |
| | 2) Pd/C |
| Hydrogenation | 1) H$_2$/HCl |
| Filtration/pH adjustment | 1) H$_2$O/NaOH |
| Concentration | 1) EtOH |
| | 2) AcOEt |

H-Ser(tBu)-4Aph(L-Hor)-D-4Aph(tBuCbm)-Leu-Lys(iPr,Boc)-Pro-D-Ala-NH$_2$ [23]

| | |
|---|---|
| Suspension | 1) AcOEt |
| | 2) HOBt |

Ac-D-2Nal-D-4Cpa-D-3Pal-ONa [7]

| | |
|---|---|
| Dissolution | 1) DMSO |
| Reaction | 1) DCC/AcOEt |
| | 2) H$_2$O/DMSO |
| Filtration | 1) AcOEt/DMSO |
| | 2) n-BuOH |
| Extraction | 1) H$_2$O acidic |
| | 2) H$_2$O alkaline |
| | 3) H$_2$O/NaCl |
| Concentration | 1) DMF |
| Precipitation | 1) H$_2$O |
| Filtration/Drying | 1) H$_2$O |

Ac-D-2Nal-D-4Cpa-D-3Pal-Ser(tBu)-4Aph(L-Hor)-D-4Aph(tBuCbm)-Leu-Lys(iPr,Boc)-Pro-D-Ala-NH$_2$ [24]

Figure 12

Step 12 (Reaction step)
Ac-D-2Nal-D-4Cpa-D-3Pal-Ser(tBu)-4Aph(L-Hor)-D-4Aph(tBuCbm)-Leu-Lys(iPr,Boc)-Pro-D-Ala-NH$_2$ [24]

| | |
|---|---|
| Deprotection | 1) TFA |
| Neutralisation | 2) H$_2$O |
| | AcONH$_4$ |
| | AcOH |
| | EtOH |
| pH adjustment | 1) TFA or AcONH$_4$ |

Step 13 (Purification and Lyophilisation)
Ac-D-2Nal-D-4Cpa-D-3Pal-Ser-4Aph(L-Hor)-D-4Aph(Cbm)-Leu-Lys(iPr,Boc)-Pro-D-Ala-NH$_2$ [24]

1) Concentration on reverse phase column and purification

2) Repurification

3) Lyophilisation

Ac-D-2Nal-D-4Cpa-D-3Pal-Ser-4Aph(L-Hor)-D-4Aph(Cbm)-Leu-Lys(iPr,Boc)-Pro-D-Ala-NH$_2$ [25]

PROCESS FOR THE MANUFACTURE OF DEGARELIX AND ITS INTERMEDIATES

This is a continuation of application Ser. No. 13/881,744, filed Jul. 9, 2013, which is a 371 of International Application PCT/EP2011/068735, filed Oct. 26, 2011, which claims the benefit of priority of European Patent Application No. 1018932.5, filed Oct. 27, 2010, all of which are incorporated herein by reference in their entireties.

TECHNICAL FIELD

The present invention relates to a liquid (or solution)-phase manufacturing process for preparing the decapeptide Degarelix, its protected precursor, and other useful intermediates. The invention further relates to polypeptides useful in the solution-phase manufacturing process and to the purification of Degarelix itself.

BACKGROUND OF THE INVENTION

Prostate cancer is a leading cause of morbidity and mortality for men in the industrialised world. Degarelix, also known as FE200486, is a third generation gonadotropin releasing hormone (GnRH) receptor antagonist (a GnRH blocker) that has been developed and recently approved for prostate cancer patients in need of androgen ablation therapy (Doehn et al., Drugs 2006, vol. 9, No. 8, pp. 565-571; WO 09846634). Degarelix acts by immediate and competitive blockade of GnRH receptors in the pituitary and, like other GnRH antagonists, does not cause an initial stimulation of luteinizing hormone production via the hypothalamic-pituitary-gonadal axis, and therefore does not cause testosterone surge or clinical flare (Van Poppel, Cancer Management and Research, 2010:2 39-52; Van Poppel et al., Urology, 2008, 71(6), 1001-1006; James, E. F. et al., Drugs, 2009, 69(14), 1967-1976).

Degarelix is a synthetic linear decapeptide containing seven unnatural amino acids, five of which are D-amino acids. It has ten chiral centers in the back bone of the decapeptide. The amino acid residue at position 5 in the sequence has an additional chiral center in the side-chain substitution giving eleven chiral centers in total. Its CAS registry number is 214766-78-6 (of free base) and it is commercially available under the Trademark Firmagon™. The drug substance is chemically designated as D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexa hydro-2,6-dioxo-4-pyrimidinyl]carbonyl]amino]-L-phenylalanyl-4-[(aminocarbonyl)amino]-D-phenylalanyl-L-leucyl-N6-(1-methylethyl)-L-lysyl-L-prolyl- and is represented by the chemical structure below (in the following also referred to as Formula I):

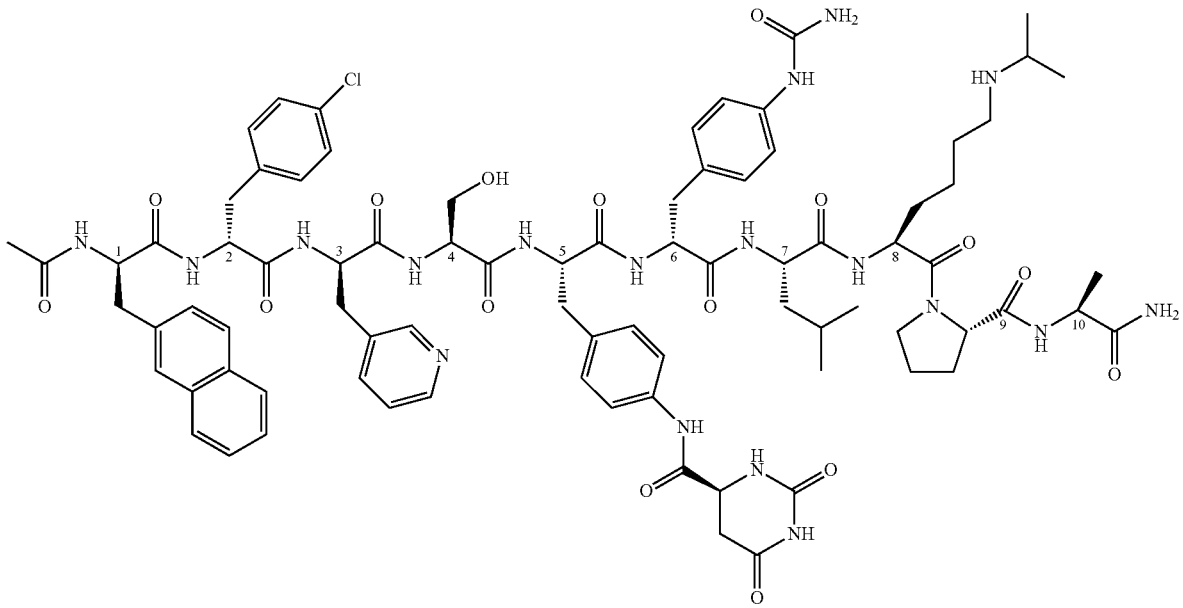 [SMILES: CC(=O)N[C@H](Cc1ccc2ccccc2c1)C(=O)N[C@H](Cc1ccc(Cl)cc1)C(=O)N[C@H](Cc1cccnc1)C(=O)N[C@@H](CO)C(=O)N[C@@H](Cc1ccc(NC(=O)[C@@H]2CC(=O)NC(=O)N2)cc1)C(=O)N[C@H](Cc1ccc(NC(N)=O)cc1)C(=O)N[C@@H](CC(C)C)C(=O)N[C@@H](CCCCNC(C)C)C(=O)N1CCC[C@H]1C(=O)N[C@@H](C)C(N)=O]

The structure of Degarelix can also be represented as:
Ac-D-2Nal-D-4Cpa-D-3Pal-Ser-4Aph(L-Hor)-D-4Aph(Cbm)-Leu-Lys(iPr)-Pro-D-Ala-$NH_2$ where Ac is acetyl, 2Nal is 2-naphthylalanine, 4Cpa is 4-chlorophenylalanine, 3Pal is 3-pyridylalanine, Ser is serine, 4Aph is 4-aminophenylalanine, Hor is hydroorotyl, Cbm is carbamoyl, Leu is leucine, Lys(iPr) is N6-isopropyllysine, Pro is proline and Ala is alanine. For the purposes of describing this invention, each amino acid in Degarelix will be given the shorthand notation as follows:

$AA_1$ is D-2Nal, $AA_2$ is D-4Cpa, $AA_3$ is D-3Pal, $AA_4$ is Ser, $AA_5$ is 4Aph(L-Hor), $AA_6$ is D-Aph(Cbm), $AA_7$ is Leu, $AA_8$ is Lys(iPr), $AA_9$ is Pro and $AA_{10}$ is D-Ala.

Thus, as an example, Degarelix can be represented as Ac-$AA_1$-$AA_{10}$-$NH_2$, the tetrapeptide Ac-D-2Nal-D-4Cpa-D-3Pal-Ser can be represented as Ac-$AA_1$-$AA_4$ and the hexapeptide 4Aph(L-Hor)-D-4Aph(Cbm)-Leu-Lys(iPr)-Pro-D-Ala-$NH_2$ as $AA_5$-$AA_{10}$-$NH_2$.

Degarelix has previously been prepared using Boc-solid phase peptide synthesis (SPPS) methodology as reported in WO 98/46634 and Jiang et al., J. Med. Chem. 2001, 44, 453-467. Basically, Boc-protected D-Ala is first coupled to MBHA resin in dimethylformamide (DMF)/$CH_2Cl_2$ using diisopropylcarbodiimide (DIC) and 1-hydroxybenzotriazole (HOBt) as activating or coupling agents. Once D-Ala is coupled to the resin, synthesis proceeds by washing, deblocking and then coupling the next amino acid residue until the decapeptide has been completed. The side chain primary amino groups of 4Aph in the 5-position and of D-4Aph in the 6-position are protected by Fmoc when they are added and modified with L-Hor and Cbm respectively before the next amino acid in the chain is added. This requires the additional steps of first removing the side-chain protection with piperdine, reacting the newly freed amino group on the peptidoresin with tert-butyl isocyanate or L-hydroorotic acid, ensuring that the reaction is complete with a ninhydrin test and then washing the peptidoresin before adding the next amino acid residue (see also Sorbera et al., Drugs of the Future 2006, Vol. 31, No. 9, pp 755-766).

While Boc-SPPS methodology has afforded sufficient quantities of Degarelix until now, the growing demand for this polypeptide means that ever larger quantities are required. Boc-SPPS, which requires HF cleavage, is not suited to large scale industrial synthesis. Indeed, WO 98/46634 mentions that SPPS is only suitable for limited quantities of up to 1 kg while classical peptide solution synthesis, or liquid phase peptide synthesis (LPPS), is preferred for larger quantities of product. WO 98/46634 does not specify how such synthesis should be performed. While the existence of a liquid phase peptide synthesis of Degarelix has been reported [EMEA Report: Assessment Report for Firmagon™ (Degarelix): Doc. Ref. EMEA/CHMP/635761/2008], as of now no details of such a process have been publically disclosed.

WO 97/34923 and WO 99/26964 are documents concerned with liquid phase processes for the preparation of biologically active peptides. WO 99/26964 is particularly concerned with the liquid phase synthesis of decapeptides having activity as GnRH antagonists. WO 99/26964 lists a number of inherent limitations of the SPPS methodology for producing GnRH antagonists including the limited capacity of the resin, the large excess of reagents and amino acids required, as well as the need to protect all reactive side chains such as the hydroxy group in Ser, the aromatic amino groups in Aph and D-Aph, the ε-i-propylamino group in Lys(i-Pr). WO 99/26964 proposes a liquid phase process which involves first preparing the central peptide fragments of the 5 and 6 positions of a decapeptide with the side chains fully elaborated and then assembling the peptide through a "4-2-4", "3-3-4" or "3-4-3" fragment assembly pattern. For example, in the preparation of the GnRH antagonist Azaline B, a tetrapeptide is coupled with a hexapeptide to form the desired decapeptide. When the same fragment assembly pattern is attempted for Degarelix, racemisation of the Ser amino acid ($AA_4$) occurs resulting in about 20% impurity of L-Ser. This impurity carries over into the final decapeptide and is difficult to remove. Furthermore, when preparing the tetrapeptide $AA_1$-$AA_4$ by adding the Ser unit to the tripeptide $AA_1$-$AA_3$ following the procedure described in WO 99/26964, tetrabutylammonium ions from the hydrolysis of the benzyl ester group could not be removed completely during the subsequent operations and were carried through to the final product. It was further found that in the Degarelix synthesis, the L-hydroorotyl group rearranges to its hydantoinacetyl analogue when L-dihydroorotic acid is coupled with 4 Amp to prepare $AA_5$. These and other problems with the solution-phase synthesis of Degarelix have now been overcome and a new solution-phase polypeptide synthesis of this decapeptide is disclosed herein for the first time.

SUMMARY OF THE INVENTION

The problems of SSPS methods for preparing Degarelix and the drawbacks of LLPS methods as described in WO 97/34923 and WO 99/26964 have now been overcome and are the subject of this invention.

In general, this invention relates to a liquid-phase synthesis of the decapeptide Degarelix.

In one aspect, the invention relates to a liquid-phase process for preparing Degarelix having the formula Ac-$AA_1$-$AA_{10}$-$NH_2$ or a pharmaceutically acceptable salt or solvate thereof, comprising the step of subjecting a Degarelix precursor according to the following formula II, or a salt or solvate thereof to a treatment with a cleaving agent:

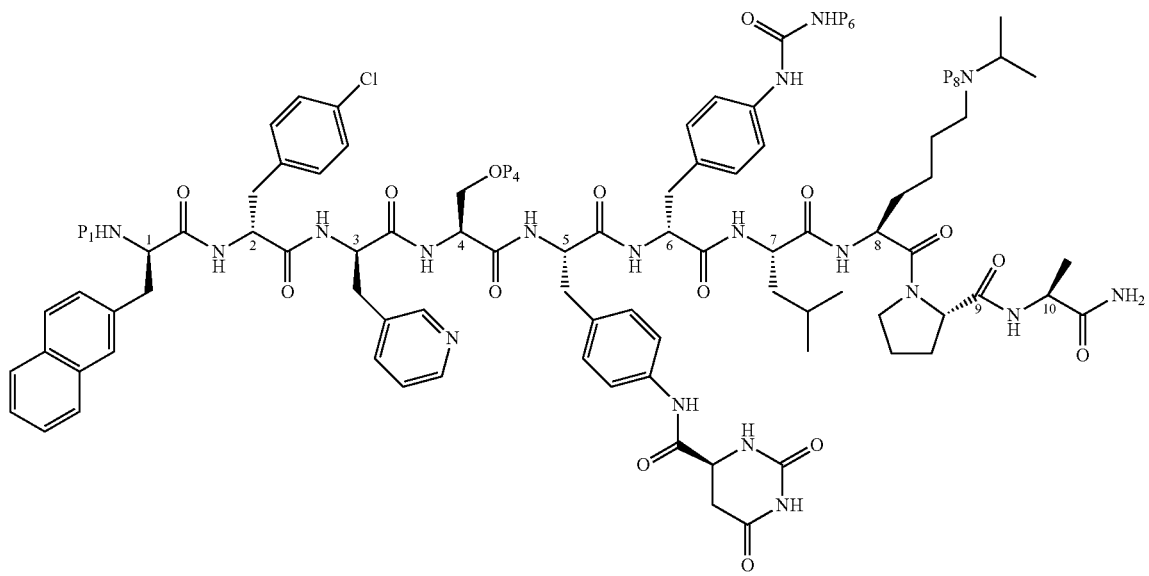

The compound of Formula II thus corresponds to $$(P_1)AA_1\text{-}AA_2\text{-}AA_3\text{-}AA_4(P_4)\text{-}AA_5\text{-}AA_6(P_6)\text{-}AA_7\text{-}AA_8(P_8)\text{-}AA_9\text{-}AA_{10}\text{-}NH_2 \quad (II)$$

where $AA_1$ to $AA_{10}$ are the same as for formula (I),
$P_1$ is an amino protecting groups or acetyl;
$P_4$ is hydrogen or a hydroxyl protecting group, preferably a hydroxyl protecting group;
$P_6$ is hydrogen or an amino protecting groups; preferably an amino protecting groups; and
$P_8$ is an amino protecting group.

Preferably, the protecting group $P_1$, if present, is orthogonal to $P_8$, i.e. both protecting groups can be cleaved independently.

In a preferred embodiment, $P_1$ is acetyl, and each of $P_4$ and $P_8$ are protecting groups that can be cleaved in a single step, and $P_6$ is hydrogen or a protecting group that can be cleaved together with the protecting groups $P_4$ and $P_8$. The cleavage of the protecting groups is preferably carried out by treating the precursor of formula II with trifluoroacetic acid (TFA). It is particularly preferred that $P_4$, $P_6$, and $P_8$ are protecting groups selected from tert-butyl (tBu) and t-butyloxycarbonyl (Boc), and most preferred is a precursor of formula II wherein $P_4$ is tBu, $P_6$ is hydrogen or tBu, and $P_8$ is Boc.

The present invention also relates to a process for the liquid-phase manufacture of the intermediate represented by formula (II) or pharmaceutically acceptable salt or solvate thereof, comprising the step of coupling a first polypeptide represented by formula (III)

$$(P_1)AA_1\text{-}AA_2\text{-}AA_3 \quad (III)$$

or a salt thereof, with a second polypeptide represented by formula (IV)

$$AA_4(P_4)\text{-}AA_5\text{-}AA_6(P_6)\text{-}AA_7\text{-}AA_8(P_8)\text{-}AA_9\text{-}AA_{10}\text{-}NH_2 \quad (IV)$$

or salt thereof, in a liquid reagent medium in the presence of a peptide coupling reagent, optionally together with an organic amine base, to form a decapeptide represented by formula (II). In this case $AA_1$ to $AA_{10}$, $P_4$, $P_6$ and $P_8$ are the same as for formula (II).

The salts include acid salts such as hydrochlorides and basic salts such as alkali metal salts, alkaline earth metal salts, and ammonium salts.

According to the invention, the second polypeptide represented by formula (IV) may be prepared by eliminating the protective group $P_N$ from the following compound (IVa):

$$(P_N)AA_4(P_4)\text{-}AA_5\text{-}AA_6(P_6)\text{-}AA_7\text{-}AA_8(P_8)\text{-}AA_9\text{-}AA_{10}\text{-}NH_2 \quad (IVa)$$

$P_N$ is preferably an N-terminal amino protecting group and more preferably a protecting group that can be eliminated by hydrogenation such as benzyloxycarbonyl.

The compound of formula (IVa) may be obtained by coupling a polypeptide represented by formula (V) with a polypeptide represented by formula (VI)

$$(P_N)AA_4(P_4)\text{-}AA_5\text{-}AA_6(P_6)\text{-}AA_7 \quad (V)$$

$$AA_8(P_8)\text{-}AA_9\text{-}AA_{10}\text{-}NH_2 \quad (VI)$$

or salts of these compounds, where $AA_4$ to $AA_{10}$, $P_N$, $P_4$, $P_6$ and $P_8$ are the same as for formula (IVa).

The invention also relates to the polypeptides represented by formulae (II) to (VI) which are useful in the liquid-phase manufacturing process of the invention.

FIGURES

Figure 3:
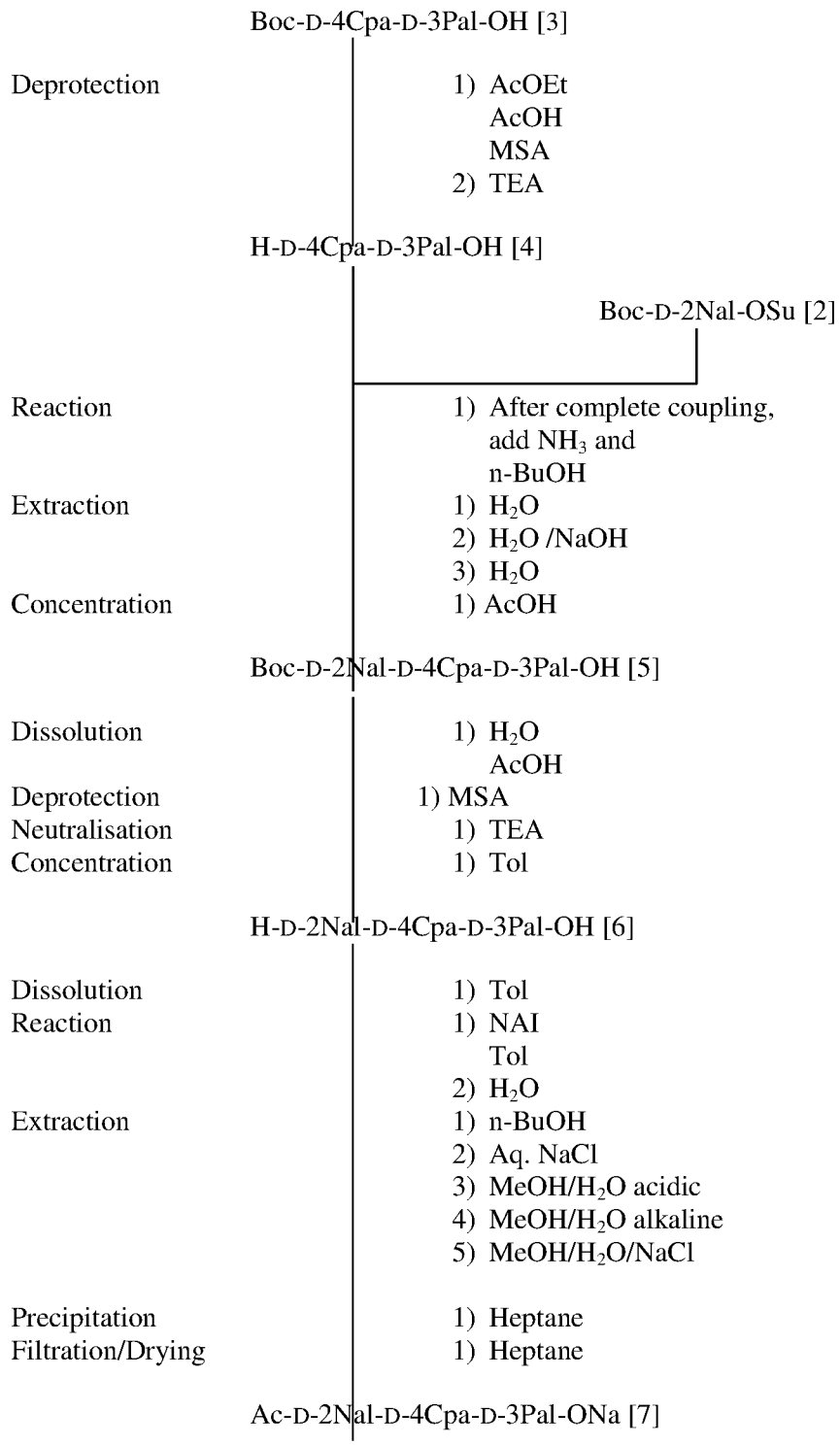
Figure 4:
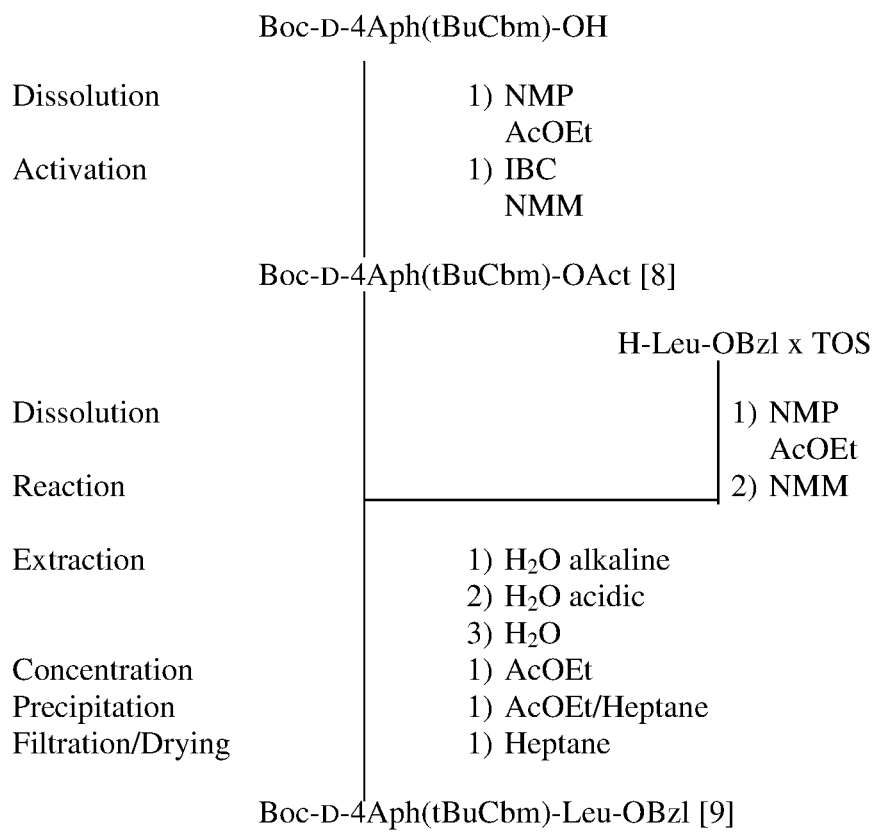
Figure 5:
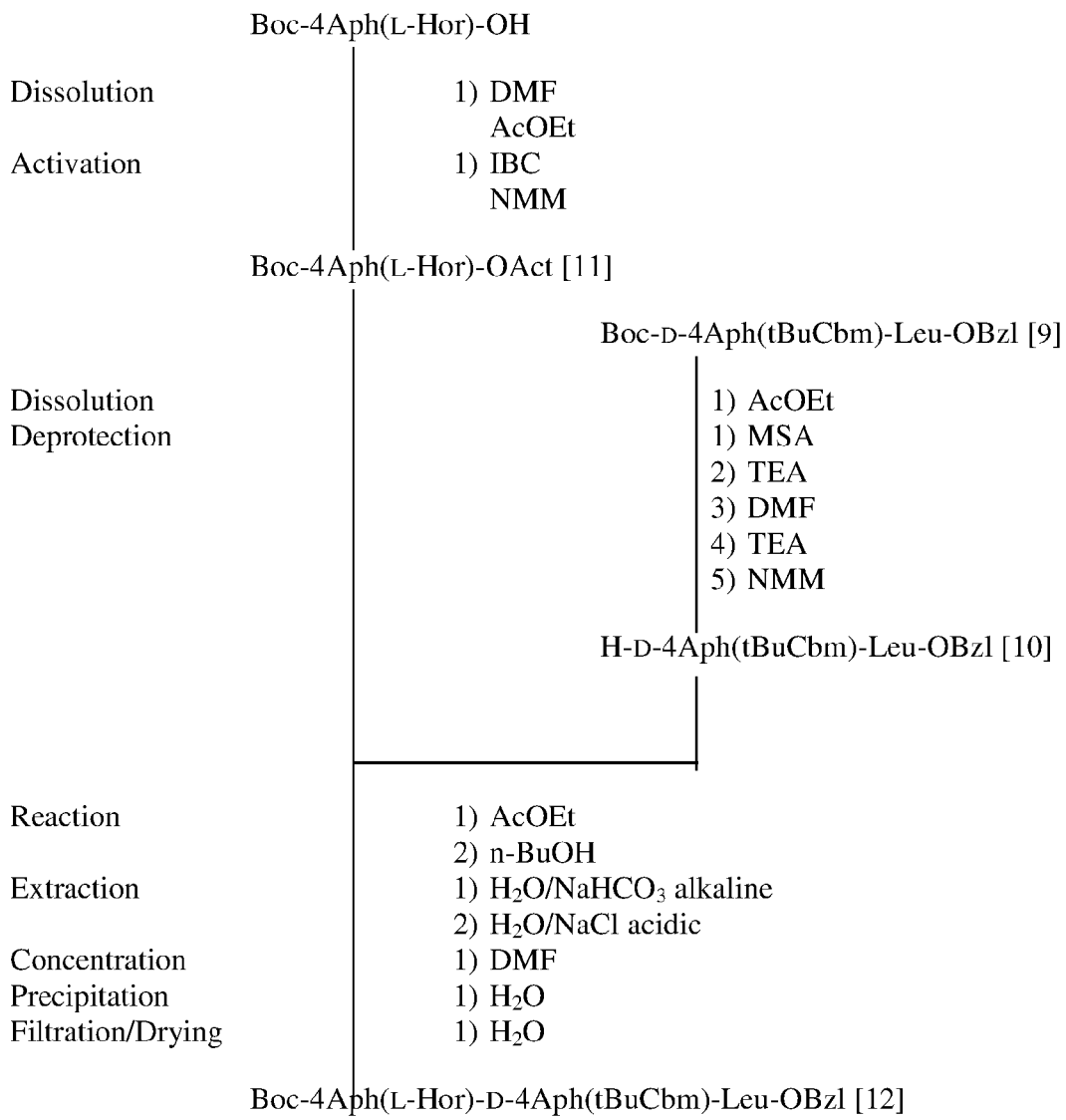
Figure 7:
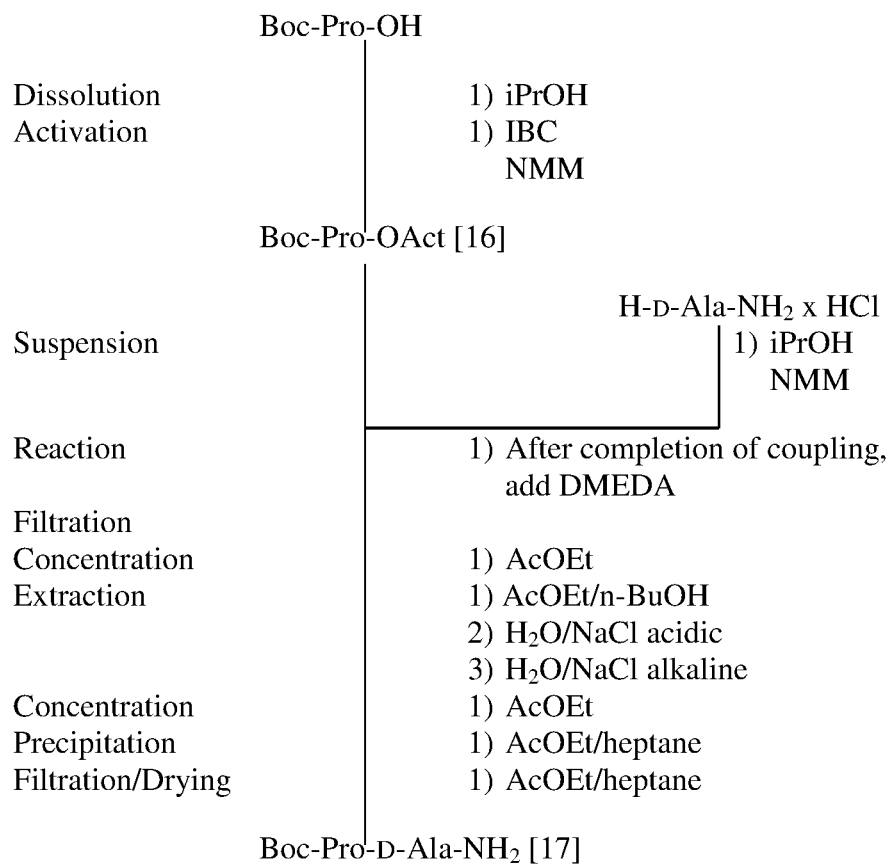
Figure 8:
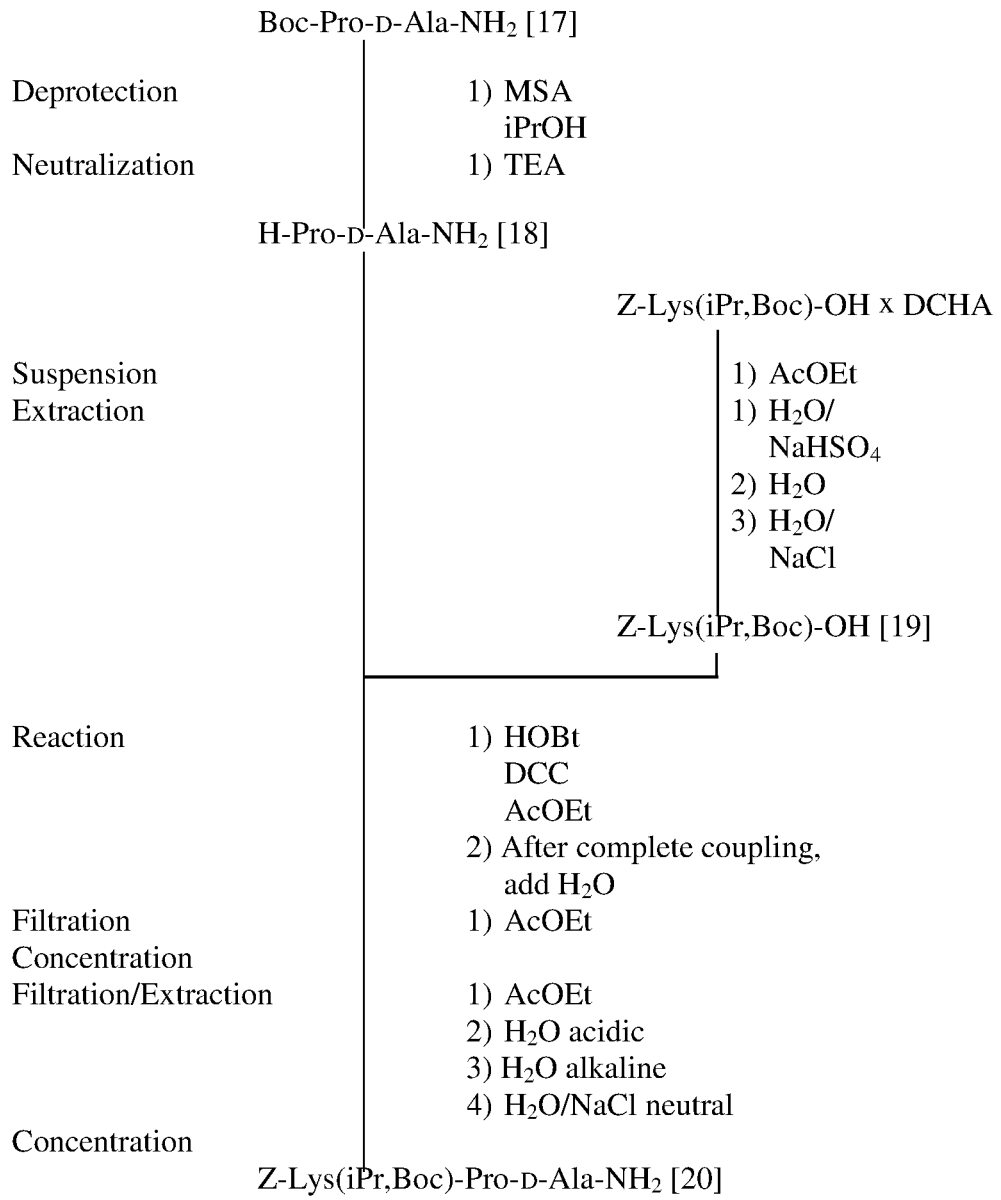

FIG. 1 shows a flow diagram for the synthesis of a derivatives of $AA_1$ and $AA_2$ for the peptide synthesis.
FIG. 2 shows a flow diagram for the synthesis of a derivative of $AA_2$-$AA_3$ for the peptide synthesis.
FIG. 3 shows a flow diagram for the synthesis of Ac-$AA_1$-$AA_3$.
FIG. 4 shows a flow diagram for the synthesis of a derivative of $AA_6$-$AA_7$.
FIG. 5 shows a flow diagram for the synthesis of a derivative of $AA_5$-$AA_7$.
FIG. 6 shows a flow diagram for the synthesis of Z-$AA_4$-$AA_7$.
FIG. 7 shows a flow diagram for the synthesis of $AA_9$-$AA_{10}$.
FIGS. 8 and 9 show a flow diagram for the synthesis of Z-$AA_8$-$AA_{10}$.
FIG. 10 shows a flow diagram for the synthesis of Z-$AA_4$-$AA_{10}$.
FIG. 11 shows a flow diagram for the synthesis of the precursor of formula II.
FIG. 12 shows a flow diagram for the synthesis of Degarelix from the precursor of formula II and the purification and lyophilisation.

DETAILED DESCRIPTION OF THE INVENTION

The present invention will now be described in more detail.

Deprotection Step

In a first aspect, the present invention relates to a liquid-phase process for preparing Degarelix having the formula Ac-$AA_1$-$AA_{10}$-$NH_2$ or a pharmaceutically acceptable salt or solvate thereof. The process comprises the step of cleaving the protecting groups ($P_4$), ($P_6$), and ($P_8$), if present, from the Degarelix precursor according to formula II (($P_1$)$AA_1$-$AA_2$-$AA_3$-$AA_4$($P_4$)-$AA_5$-$AA_6$($P_6$)-$AA_7$-$AA_8$($P_8$)-$AA_9$-$AA_{10}$-$NH_2$), or a salt or solvate thereof, in an organic solution comprising the precursor and a cleaving agent dissolved therein.

$AA_1$ to $AA_{10}$ in formula II have the same meaning as in formula (I), and $P_1$ is an amino protecting groups or acetyl, preferably acetyl.

$P_8$ is an amino protecting group. Preferably, $P_8$ is any side chain protecting group known in the art such as those described in E. Gross & J. Meienhofer, The Peptides: Analysis, Structure, Biology, Vol. 3: Protection of Functional Groups in Peptide Synthesis (Academic Press, N.Y., 1981). Suitable examples include 9-fluorenylmethyloxycarbonyl (Fmoc), benzyloxycarbonyl (Cbz or Z), and substituted Cbz, such as, e.g., 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; aliphatic urethane-type protecting groups, such as t-butyloxycarbonyl (Boc), t-amyloxycarbonyl, isopropyloxycarbonyl, 2-(p-biphenylyl)-isopropyloxycarbonyl, and the like; cycloalkyl urethane-type protecting groups, such as cyclopentyloxycarbonyl, adamantyloxycarbonyl, and cyclohexyloxycarbonyl; allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2- oxycarbonyl](Ddz), 2,2,2-trichloroethyloxycarbonyl (Troc), biphenylylisopropyloxycarbonyl (Bpoc), and o-nitrobenzyloxycarbonyl. Preferred protecting groups are Fmoc, Boc and Alloc with Boc being most preferred.

$P_4$ is hydrogen or a hydroxyl protecting group, preferably a hydroxyl protecting group. The hydroxyl group of Ser ($P_4$) is preferably a $C_4$-$C_6$ alkyl (e.g. t-butyl, cyclohexyl), acetyl (Ac), trityl, benzyl, a benzyl ether such as p-methoxybenzyl, or other substituted benzyls such as p-nitrobenzyl, p-chlorobenzyl, o-chlorobenzyl, and 2,6-dichlorobenzyl, tetrahydropyranyl, tri($C_1$-$C_6$)alkylsilyl, 2-methoxyethoxymethyl (MEM), 4-dimethylcarbamoylbenzyl and O-phenoxyacetyl ethers.

Particularly preferred are t-butyl, benzyl and 9-fluorenylmethyl ethers, t-butyl being most preferred.

$P_6$ is hydrogen or an amino protecting groups, preferably an amino protecting groups.

trifluoracetic acid (TFA), HCl, or methanesulfonic acid, particularly for t-butyl ether as a protecting group
$H_2$/Pd—C, HF, or trifluoromethane-sulfonic acid, particularly for benzyl ether as a protecting group, and
$SiCl_4$/anisol, particularly for 2-(methylsulfinyl)benzylether as a protecting group;

Preferred cleaving agents for the amino protecting group $P_8$ are:
trifluoracetic acid (TFA), HCl, or methanesulfonic acid, particularly for t-butyl carbamates as protecting group
$H_2$/Pd—C, HF, or trifluoromethane-sulfonic acid, particularly for benzyl carbamates as protecting group, and
Piperidine, DBU and DEA, particularly for Fmoc as protecting group Preferred solvents include DCM, DMF, NMP, dioxane, EtOH, Neat HF, and TFA.

Particularly preferred are the different cleavage conditions indicated in the following table 1:

TABLE 1

Cleavage conditions

| Protecting group | | Protected | | |
|---|---|---|---|---|
| Abbreviation | Name | group | Cleavage reagent | Solvent |
| t-Bu | t-Butyl ethers and esters | —OH and —$CO_2$H | TFA<br>HCl<br>Methanesulfonic acid | DCM<br>Dioxane<br>DCM |
| Bzl | Benzyl ethers and esters | —OH and —$CO_2$H | $H_2$/Pd—C<br>HF<br>Trifluoromethane-sulfonic acid | EtOH/water<br>Neat<br>DCM |
| MsOb | 4-(Methylsulfinyl)-benzyl ether | —OH | $SiCl_4$/anisol | TFA |
| Cbz or Z | Benzyloxycarbonyl | —$NH_2$ | $H_2$/Pd—C<br>HF<br>Trifluoromethane-sulfonic acid | EtOH/Water/acid<br>Neat<br>DCM |
| Boc | tert-Butoxy-carbonyl | —$NH_2$ | TFA<br>HCl<br>Methanesulfonic acid | DCM<br>Dioxane<br>DCM |
| Fmoc | 9-Fluorenylmethoxy-carbonyl | —$NH_2$ | piperidine<br>DBU (1,8-diazabicyclo[5.4.0]-undec-7-ene)<br>DEA (diethylamine) | DMF<br>DMF<br>DMF |
| Trt | Trityl (Trt) | —OH —$NH_2$ | 1% TFA-DCM | DCM |
| TBDMS | Tert-butyl-dimethyl-silyl | —OH | TFA<br>ACOH-THF—$H_2$O (3:1:1), 18 h | THF |
| Cyclohexyl (CHX or $CH_X$) | Cyclohexyl | —OH | HF or TFSMA | Neat HF or DCM |

Preferred protecting groups include $C_4$-$C_6$ alkyl (e.g. t-butyl, cyclohexyl), acetyl (Ac), trityl, benzyl, a benzyl ether such as p-methoxybenzyl, or other substituted benzyls such as p-nitrobenzyl, p-chlorobenzyl, o-chlorobenzyl, and 2,6-dichlorobenzyl, tetrahydropyranyl, tri($C_1$-$C_6$)alkylsilyl, 2-methoxyethoxymethyl (MEM), 4-dimethylcarbamoylbenzyl and O-phenoxyacetyl ethers. Particularly preferred are t-butyl, benzyl and 9-fluorenylmethyl ethers, t-butyl being most preferred.

The cleaving agent used to remove the protecting groups depends on the nature of the protecting group and are well known in the art.

Preferred cleaving agents for the Ser hydroxyl protecting group $P_4$ are:

Reference: Chem. Rev. 2009, 109, 2465-2504 (by Albert Isidro-Llobet)

Typically, the precursor of formula II is dissolved in a cleaving agent, preferably TFA, with or without an additional solvent, at room temperature (20 to 25° C.) for 20 to 30 hours, preferably 24 hours. When the protecting group has been removed (preferably the conversion is >95% yield, most preferably >99%), the crude Degarelix is then preferably poored into a buffered water-ethanol mixture to provide a buffered solution of crude degarelix for subsequent purification. The preferred pH is preferably in the range of 2 to 4, more preferably in the range of 2.5 to 3.5, and most preferably approximately 3.

Specific embodiments of the deprotection step are shown in FIG. 12 and Example 4 (see Step 12).

Purification and Lyophilization

The solution of crude degarelix is preferably purified using chromatographic techniques such as preparative reverse phase chromatography (RPC).

The resulting product is then preferably lyophilized.

3+7 Coupling

In a further aspect, the present invention also relates to a process for the liquid-phase manufacture of the intermediate represented by formula (II) or pharmaceutically acceptable salt or solvate thereof, comprising the step of coupling a first polypeptide represented by formula (III)

$$(P_1)AA_1\text{-}AA_2\text{-}AA_3 \qquad (III)$$

or a salt thereof, with a second polypeptide represented by formula (IV)

$$AA_4(P_4)\text{-}AA_5\text{-}AA_6(P_6)\text{-}AA_7\text{-}AA_8(P_8)\text{-}AA_9\text{-}AA_{10}\text{-}NH_2 \qquad (IV)$$

or a salt thereof, in a liquid reagent medium in the presence of a peptide coupling reagent and optionally an organic amine base, to form a decapeptide represented by formula (II). In this case $AA_1$ to $AA_{10}$, $P_1$, $P_4$, $P_6$ and $P_8$ are the same as for formula (II). The salts include acid salts such as hydrochlorides and basic salts such as alkali metal salts, alkaline earth metal salts, and ammonium salts.

The coupling reaction is performed in an organic solution where the two peptides and a peptide coupling reagent and optionally an organic amine base are dissolved therein. A peptide coupling additive and/or an organic amine may also be present.

The organic solvent, peptide coupling reagent, peptide coupling additive and organic amine base may be any of those known in the art of LPPS.

Typical organic solvents are THF, NMP (N-methyl pyrrolidone), DCM, DMF, DMSO, and mixtures thereof. The most preferred solvent is DMSO.

Typical peptide coupling reagents are one or more of o-(7-azabenzotriazol-1-yl)-1,1,3,3-tetramethyluronium hexafluorophosphate (HATU), o-(benzotriazol-1-yl)-1,1,3,3-tetramethyluronium hexafluorophosphate (HBTU), o-(benzotriazol-1-yl)-1,1,3,3-tetramethyluronium tetrafluoroborate (TBTU), benzotriazole-1-yl-oxy-tris(dimethylamino)phosphonium hexafluorophosphate (BOP), benzotriazole-1-yl-oxy-tris-pyrrolidinophosphonium hexafluorophosphate (PyBOP), N,N-bis-(2-oxo-3-oxazolidinyl)phosphonic dichloride (BOP—Cl), bromo-tris-pyrrolidino-phosphonium hexafluorophosphate (PyBroP), isobutylchloroformate (IBCF), 1,3 dicyclohexylcarbodiimide (DCC), 1,3-diisopropyl-carbodiimide (DIC), 1-(dimethylaminopropyl)-3-ethylcarbodiimide hydrochloride (WSCDI), N-ethoxycarbonyl-2-ethoxy-1,2-dihydroquinoline (EEDQ), isopropylchloroformate (IPCF), 2-(5-norbornen-2,3-dicarboximido)-1,1,3,3-tetramethyluronium tetrafluoroborate (TNTU), propane phosphonic acid anhydride (PPAA) and 2-succinimido-1,1,3,3-tetramethyluronium tetrafluoroborate (TSTU).

A preferred coupling agent is DCC. DCC is preferably used without an organic amine. In a particularly preferred embodiment, DCC is used in combination with DMSO. DCC is preferably used in an amount of 1.3 to 2, most preferably 1.4 to 1.6 equivalents with respect to the tripeptide.

Another preferred coupling agent is DIC, which is preferably used in combination with 6-chloro-HOBt, optionally together with copper salts.

Typical peptide coupling additives are 1-hydroxy-1H-benzotriazole (HOBt), 6-chloro-HOBt, and 1-hydroxy-7-azabenzotriazole (HOAt).

Typical organic amine bases are NMM, DIPEA, TEA, and collidine.

It is particularly preferred to carry out the coupling reaction using DMSO as solvent and DCC as coupling agent.

Specific embodiments of the coupling step are shown in FIG. 11 and Example 4 (see Step 11).

Synthesis of the Heptapeptide

The compound of formula IV, i.e. $AA_4(P_4)\text{-}AA_5\text{-}AA_6(P_6)\text{-}AA_7\text{-}AA_8(P_8)\text{-}AA_9\text{-}AA_{10}\text{-}NH_2$, is preferably obtained by eliminating the protective group $P_N$ of the following compound IVa:

$$(P_N)AA_4(P_4)\text{-}AA_5\text{-}AA_6(P_6)\text{-}AA_7\text{-}AA_8(P_8)\text{-}AA_9\text{-}AA_{10}\text{-}NH_2 \qquad (IVa)$$

While $AA_4$ to $AA_{10}$, $P_4$, $P_6$, and $P_8$ have the same meaning as above, $P_N$ is an N-terminal amino protecting group. In a preferred embodiment, $P_N$ is a protecting group that can be eliminated by hydrogenation, e.g. using hydrogen and a palladium catalyst (such as Pd/C). The most preferred protecting group $P_N$ is benzyloxycarbonyl (Z).

Specific embodiments of the elimination step of $P_N$ are shown in FIG. 11 and Example 4 (see Step 11).

The compound of formula (IVa) may be obtained by coupling a polypeptide represented by formula (V) with a polypeptide represented by formula (VI)

$$(P_N)AA_4(P_4)\text{-}AA_5\text{-}AA_6(P_6)\text{-}AA_7 \qquad (V)$$

$$AA_8(P_8)\text{-}AA_9\text{-}AA_{10}\text{-}NH_2 \qquad (VI)$$

or salts of one or both of these compounds, where $AA_4$ to $AA_{10}$, $P_4$, $P_6$ and $P_8$ are the same as for formula (IVa). The coupling reaction is performed in an organic solution where the two peptides and a peptide coupling reagent are dissolved therein. A peptide coupling additive and/or an organic amine may also be present. The same peptide coupling reagents, organic solvents, peptide coupling additives and organic amines as described above may be used. In a preferred embodiment, DCC is used as a coupling reagent, optionally with ethyl acetate as solvent.

Synthesis of the Tetrapeptide of Formula V

In a preferred embodiment, the tetrapeptide of formula V, i.e. $(P_N)AA_4(P_4)\text{-}AA_5\text{-}AA_6(P_6)\text{-}AA_7$, is prepared by a process comprising the following steps:

(a) providing $(P_{N2})AA_5\text{-}AA_6(P_6)\text{-}AA_7(P_C)$, wherein $P_6$ has the same meaning as above in formula IVa, $(P_{N2})$ is an N-terminal amino protecting group or hydrogen, and $(P_C)$ is a C-terminal carboxyl protecting group that can be cleaved by hydrogenation;

(b) removing the amino protecting group $(P_{N2})$, if present;

(c) hydrogenating $H\text{-}AA_5\text{-}AA_6(P_6)\text{-}AA_7(P_C)$ to obtain $H\text{-}AA_5\text{-}AA_6(P_6)\text{-}AA_7$; and (d) reacting $H\text{-}AA_5\text{-}AA_6(P_6)\text{-}AA_7$ with an activated ester of $(P_N)AA_4(P_4)$ to provide $(P_N)AA_4(P_4)\text{-}AA_5\text{-}AA_6(P_6)\text{-}AA_7$, wherein $(P_4)$ is a hydroxyl protecting group or hydrogen, $P_6$ is hydrogen or an amino protecting group, and $P_N$ is a protecting group that can preferably be eliminated by hydrogenation, e.g. using hydrogen and a palladium catalyst (such as Pd/C).

The most preferred protecting group $P_N$ is benzyloxycarbonyl (Z).

The preferred activated ester of $(P_N)AA_4(P_4)$ is a 4-nitrophenyl ester (ONp).

Hence, preferably, the benzyl ester is removed in the AA5-AA7 intermediate to provide both N- and C-unprotected AA5-AA7. This tripeptide is then reacted with pre-activated serine (e.g. Z-Ser(tBu)-ONp).

Degarelix Manufacture

The present invention thus relates to the manufacture of Degarelix, the above-discussed deprotection step being an essential step of this manufacture. In a preferred embodiment, this deprotection step follows the 3+7 coupling discussed above. In an even more preferred embodiment, the 3+7 coupling follows the synthesis of the heptapeptide discussed above, i.e. the process comprises the following steps:

a) Synthesis of $AA_4(P_4)$-$AA_5$-$AA_6(P_6)$-$AA_7$-$AA_8(P_8)$-$AA_9$-$AA_{10}$-$NH_2$, or a salt or solvate thereof;

b) Coupling of $AA_4(P_4)$-$AA_5$-$AA_6(P_6)$-$AA_7$-$AA_8(P_8)$-$AA_9$-$AA_{10}$-$NH_2$ and $(P_1)AA_1$-$AA_2$-$AA_3$ to provide $(P_1)AA_1$-$AA_2$-$AA_3$-$AA_4(P_4)$-$AA_5$-$AA_6(P_6)$-$AA_7$-$AA_8(P_8)$-$AA_9$-$AA_{10}$-$NH_2$), or a salt or solvate thereof;

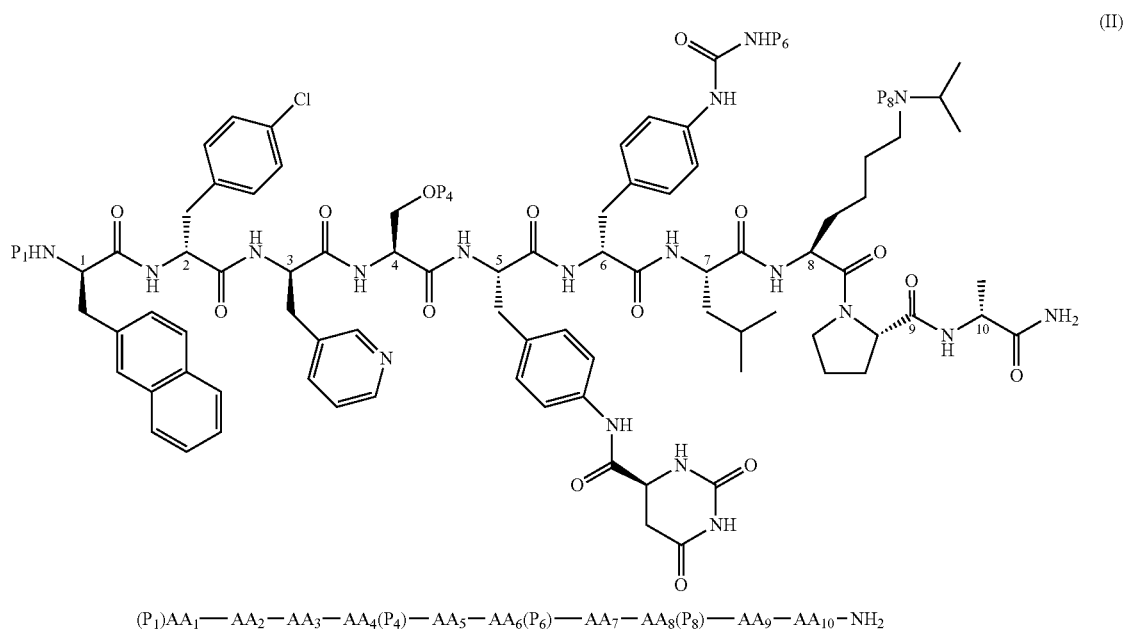

$(P_1)AA_1$—$AA_2$—$AA_3$—$AA_4(P_4)$—$AA_5$—$AA_6(P_6)$—$AA_7$—$AA_8(P_8)$—$AA_9$—$AA_{10}$-$NH_2$ c) Deprotection of $(P_1)AA_1$-$AA_2$-$AA_3$-$AA_4(P_4)$-$AA_5$-$AA_6(P_6)$-$AA_7$-$AA_8(P_8)$-$AA_9$-$AA_{10}$-$NH_2$), or a salt or solvate thereof to provide degarelix, or a solvate or salt thereof.

$AA_1$ to $AA_{10}$ and $P_1$, $P_4$, $P_6$, and $P_8$ have the same meanings as defined above.

In a particularly preferred embodiment, $P_1$ is acetyl;

$P_4$ is a protecting group that is cleavable with TFA, preferably tBu;

$P_6$ is a hydrogen or a protecting group that is cleavable with TFA, preferably tBu;

$P_8$ is a protecting group that is cleavable with TFA, preferably Boc.

In the most preferred embodiment, the heptapeptide is produced using the heptapeptide synthesis described above. Moreover, the deprotection step is preferably followed by the purification and lyophilisation methods described above.

In the synthesis of degarelix or its precursors, and particularly in all steps containing a peptide with the hydrooro-tyl moiety, the pH is preferably kept below 9, preferably below 8.5, even more preferred being below 8. It is preferred to use a weak base such as NaHCO3 for pH adjustment. It is particularly preferred that all extractions after the coupling steps are carried out within a pH range of 2 to 9, preferably 2.5 to 8 (see steps 6, 7, 10, and 11 in the experimental section). It is additionally preferred to add and C4-5 aliphatic alcohol such as n-butanol or 2-butanol prior to the extraction or washing step.

Intermediates

The invention also relates to the polypeptides represented by formulae (II) to (VI) which are useful in the liquid-phase manufacturing process of the invention.

Preferred Embodiments of Formula (II)

TABLE 2

| Compound | $P_1$ | $P_4$ | $P_6$ | $P_8$ |
|---|---|---|---|---|
| IIa | Ac | tBu | tBu | Fmoc |
| IIb | Ac | tBu | tBu | Boc |
| IIc | Ac | H | H | Alloc |
| IId | Ac | H | H | Boc |
| IIe | Ac | tBu | H | Boc |
| IIf | Boc | tBu | tBu | Fmoc |
| IIg | Fmoc | tBu | tBu | Boc |
| IIh | Boc | tBu | H | Fmoc |
| IIi | Fmoc | tBu | H | Boc |
| IIj | Ac | H | tBu | Boc |
| IIk | Ac | H | tBu | Fmoc |
| III | Ac | H | H | Fmoc |

Preferred embodiments include salts of these compounds.
Preferred Embodiments of Formula (III)

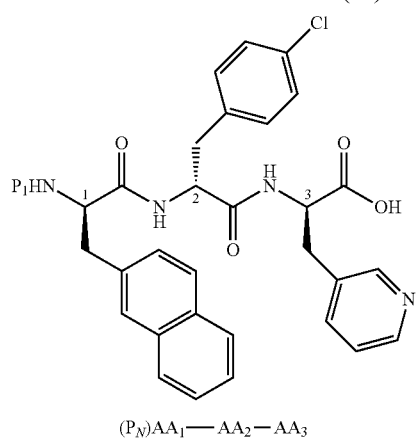

(III)

$(P_N)AA_1$—$AA_2$—$AA_3$

TABLE 3

| Compound | $P_N$ |
|---|---|
| IIIa | Ac |
| IIIb | Boc |

Preferred embodiments include salts of these compounds.
Preferred Embodiments of Formula (IV)/(IVA)

TABLE 4

| Compound | $P_4$ | $P_6$ | $P_8$ | $P_N$ |
|---|---|---|---|---|
| IVa | tBu | tBu | Fmoc | H |
| IVb | tBu | tBu | Boc | H |
| IVc | H | H | Alloc | H |
| IVd | H | H | Boc | H |
| IVe | tBu | H | Boc | H |
| IVf | H | H | Fmoc | H |
| IVg | tBu | H | Fmoc | H |
| IVh | tBu | tBu | Fmoc | Z |
| IVi | tBu | tBu | Boc | Z |
| IVj | H | H | Alloc | Z |
| IVk | H | H | Boc | Z |
| IVl | tBu | H | Boc | Z |
| IVm | H | tBu | Boc | Z |
| IVn | H | H | Fmoc | Z |
| IVo | tBu | H | Fmoc | Z |
| IVp | H | tBu | Fmoc | Z |

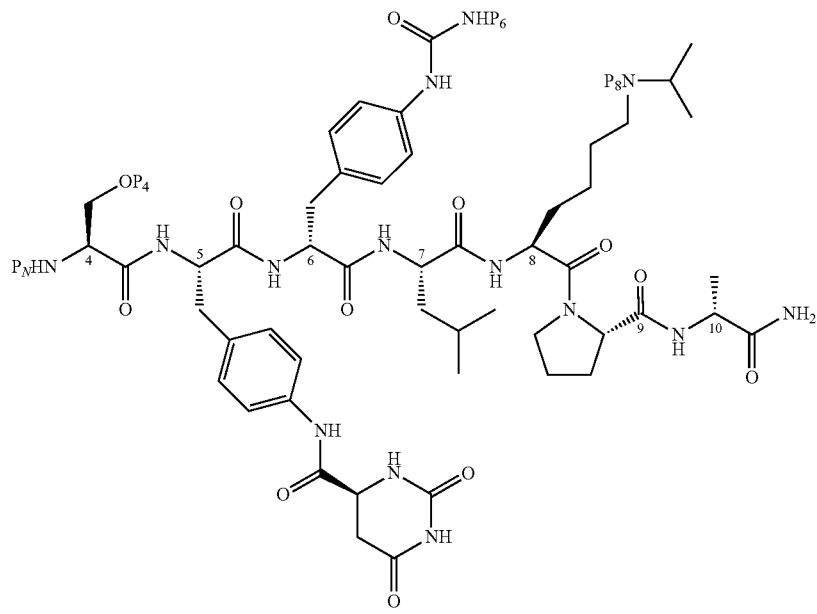

(IV)

$(P_N)AA_4(P_4)$—$AA_5$—$AA_6(P_6)$—$AA_7$—$AA_8(P_8)$—$AA_9$—$AA_{10}$-$NH_2$

Preferred embodiments include salts of these compounds.
Preferred Embodiments of Formula (V)

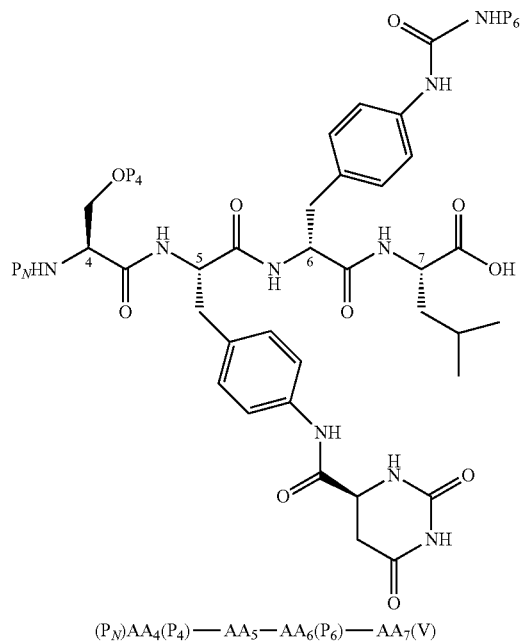

$(P_N)AA_4(P_4)$—$AA_5$—$AA_6(P_6)$—$AA_7(V)$

TABLE 5

| Compound | $P_4$ | $P_6$ | $P_N$ |
|---|---|---|---|
| Va | tBu | tBu | Z |
| Vb | tBu | H | Z |
| Vc | H | tBu | Z |
| Vd | H | H | Z |

Preferred embodiments include salts and solvates of these compounds.
Preferred Embodiments of Formula (VI)

(VI)

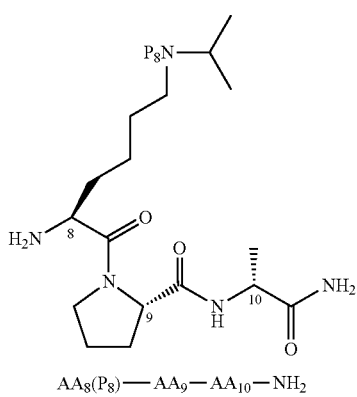

$AA_8(P_8)$—$AA_9$—$AA_{10}$—$NH_2$

TABLE 6

| Compound | $P_8$ |
|---|---|
| VIa | Boc |
| VIb | Alloc |
| VIc | Fmoc |

When a protecting group is not present, the functional group is the deprotected group (e.g. >NH).

Preferred embodiments include salts of these compounds.

EXPERIMENTAL SECTION

I. Materials Used in the Experimental Section

The materials used in the experimental section are listed below.

Chemicals:

aqueous ammonia $NH_3$ (aq)
Acetonitrile $C_2H_3N$
n-Butanol $C_4H_{10}O$
2-Butanol $C_4H_{10}O$
Isopropanol (isopropanol) $C_3H_8O$
Butyl acetate $C_5H_{12}O_2$
Ethanol, 99.9% $C_2H_6O$
Methanol $CH_4O$
Heptane $C_7H_{16}$
Purified water $H_2O$
Ethyl acetate $C_3H_8O_2$
Acetic acid $C_2H_4O_2$
Ammonium acetate $C_2H_7NO_2$
Acetyl imidazole $C_5H_6N_2O$
Triethylamine $C_6H_{15}N$
N-Methylmorpholine $C_5H_{11}NO$
N-Methylpyrrolidone $C_5H_9NO$
N,N'-Dicyclohexylcarbodiimide $C_{13}H_{22}N_2$
Dicyclohexylamine $C_{12}H_{23}N$
N,N'-Diisopropylcarbodiimide $C_7H_{14}N_2$
N,N-Dimethylethylenediamine $C_4H_{12}N$
N,N-Dimethylformamide $C_3H_7NO$
Dimethyl sulphoxide $C_2H_6OS$
1-Hydroxybenzotriazole $C_6H_5N_3O$
p-Nitrophenol $C_6H_5NO_3$
N-Hydroxysuccinimide $C_4H_5NO_3$
Isobutyl chloroformate $C_5H_9ClO_2$
Sodium chloride NaCl
Sodium hydroxide, aqueous NaOH (aq)
Hydrochloric acid, aqueous HCl (aq)
Phosphoric acid $H_3PO_4$
Sodium hydrogensulphate $NaHSO_4$
Sodium hydrogencarbonate $NaHCO_3$
Methanesulphonic acid $CH_4SO_3$
Trifluoroacetic acid $C_2HF_3O_2$
Palladium on charcoal, 5% Pd—C
Hydrogen $H_2$
Toluene $C_7H_8$ Starting Materials:

| | |
|---|---|
| N-t-Butyloxycarbonyl-D-4-chlorophenylalanine | Boc-D-4Cpa-OH $C_{14}H_{18}NO_4$ |
| N-t-Butyloxycarbonyl-D-2-naphtylalanine | Boc-D-2Nal-OH $C_{18}H_{21}NO_4$ |
| D-3-Pyridylalanine hydrochloride | H-D-3Pal-OH × 2HCl $C_8H_{12}Cl_2N_2O_2$ |
| N-α-t-Butyloxycarbonyl-N-4-(t-Butylcarbamoyl)-D-4-Aminophenylalanine | Boc-D-4Aph(tBuCbm)-OH $C_{19}H_{29}N_3O_5$ |
| N-α-t-Butyloxycarbonyl-N-4-(L-Hydroorotyl)-4-Aminophenylalanine | Boc-4Aph(L-Hor)-OH $C_{19}H_{24}N_4O_7$ |
| Leucine benzyl ester p-tosylate | H-Leu-OBzl × TOS $C_{20}H_{27}NO_5$ |
| N-Benzyloxycarbonyl-O-t-butyl-serine | Z-Ser(tBu)-OH $C_8H_{15}NO_5$ |
| N-t-Butyloxycarbonyl-proline | Boc-Pro-OH $C_{10}H_{17}NO_4$ |
| D-Alaninamide hydrochloride | H-D-Ala-NH$_2$ × HCl $C_3H_8ClNO_2$ |
| N-α-Benzyloxycarbonyl-N-ε-t-butyloxycarbonyl-N-ε-isopropyl-lysine, dicyclohexylamine salt | Z-Lys(iPr,Boc)-OH × DCHA $C_{34}H_{57}N_3O_6$ |

Example 1

Synthesis of Intermediate Ac(1-3)ONa: Ac-D-2Nal-D-4Cpa-D-3Pal-ONa[7]

Activation of Boc-D-4Cpa-OH and Isolation

Step 1 (Reaction Step)

Boc-D-4Cpa-OH (299.75 g) is dissolved in iPrOH (3.53 kg), the mixture is stirred and HOSu (0.184 kg) and DIC (0.164 kg) are added, and stirred at 0° C. for 1 hour. The precipitate is filtered off and washed with iPrOH. The solid is dried under reduced pressure to yield Boc-D-4Cpa-OSu [1].

Activation of Boc-D-2Nal-OH and Isolation

Step 2 (Reaction Step)

Boc-D-2Nal-OH (315.38 g) is dissolved in iPrOH (5.35 kg) and IBC (157.07 g) and NMM (116.7 g) are added. A mixture of water (42 mL), iPrOH (1.1 kg) and HOSu (230.14 g) is added after cooling to −10° C. together with additional NMM (10.11 g), and the mixture stirred 30 min. Water (0.82 L) is added and the precipitate is filtered off, and washed with iPrOH and dried under reduced pressure to yield Boc-D-2Nal-OSu[2].

Synthesis of Boc(2-3)OH: Boc-D-4Cpa-D-3Pal-OH

Step 3 (Reaction Step)

H-D-3Pal-OH×2 HCl (0.251 kg) and Boc-D-4Cpa-OSu [1] (0.397 kg) from step 1 are dissolved in DMSO (3.33 L) and NMM (318.8 g) is added. The mixture is stirred at 20° C. for 6 hours.

Water (17 L) is added and pH is adjusted by adding HCl to pH 4.25. The precipitate is filtered off, and dispersed in water. The obtained slurry is then filtered and washed with water. The solid is dried under reduced pressure to yield Boc-D-4Cpa-D-3Pal-OH[3].

Synthesis of Intermediate Ac(1-3)ONa: Ac-D-2Nal-D-4Cpa-D-3Pal-ONa[7](Compound of formula IIIa)

Step 4 (Reaction Step)

Boc-D-4Cpa-D-3Pal-OH [3] (447.93 g) from step 3 is dissolved in a mixture of AcOEt (3.4 L) and AcOH (675 mL), the mixture is cooled at 5° C. where after MSA (672.77 g) is added. The reaction continues at 10° C. for 2 hours and to the solution is added TEA (1214.28 g) to yield H-D-4Cpa-D-3 Pal-OH [4].

Boc-D-2Nal-OSu [2] (412.44 g) from step 2 is added to H-D-4Cpa-D-3Pal-OH [4], stirred for 24 hours at 20° C. 25% aqueous NH$_3$ (0.154 L) and n-butanol (4.5 L) are added, and the mixture is stirred at 45° C. for 1 hour.

The solution is washed with:
Water
Water at pH 9.5 (pH is adjusted while stirring with aq. NaOH)
Water AcOH (4.5 L) is added to the organic phase and the solution is concentrated to an oil under reduced pressure. The oil is re-dissolved in AcOH (4.5 L) and re-concentrated under reduced pressure to yield Boc-D-2Nal-D-4Cpa-D-3Pal-OH[5] as an oil.

Boc-D-2Nal-D-4Cpa-D-3Pal-OH [5] is dissolved in water (0.09 L) and AcOH (1.8 L). MSA (672.77 g) is added and the mixture is stirred at below 35° C. for 2 hours. The solution is neutralised with TEA (779.16 g). The solution is concentrated under reduced pressure to an oil. The oil is re-dissolved in toluene (2.5 L) and re-concentrated under reduced pressure to an oil. The last step is repeated to yield H-D-2Nal-D-4Cpa-D-3Pal-OH[6].

H-D-2Nal-D-4Cpa-D-3Pal-OH [6] is dissolved in toluene (2.0 L) and a solution of acetyl imidazole (132.14 g) in toluene (0.25 L) is added. The solution is stirred at 20° C. for 2 hours, and water (0.1 L) is added.

n-Butanol (4.5 L) is added and the organic mixture is washed at 35° C. with:
5% aqueous NaCl
Methanol and water at acidic pH 5.5 (pH is adjusted while stirring with aq. NaOH)
Methanol and water at pH 11 (pH is adjusted while stirring with aqueous NaOH)
Methanol and 10% aqueous NaCl To the stirred organic phase from the extractions, heptane (15 L) is added at 20° C. for 1 hour, and the resulting suspension is left with stirring at 20° C. for 1 hour. The precipitate is isolated by filtration, and suspended in heptane (3.5 L). The suspension is filtered again. The last washing step with heptane and the filtration is repeated. The solid is then dried under reduced pressure to yield Ac-D-2Nal-D-4Cpa-D-3Pal-ONa[7].

Specifications for Key Intermediates
Step 4 Intermediate Ac(1-3)ONa[7]

| Quality Control | Acceptance criteria |
|---|---|
| Description | "White to slightly yellow powder (visual inspection)" |
| Identification (1) | "587.2 ± 0.4Da (MS)" |
| Identification (2) | "2Nal 0.9-1.1, 4Cpa 0.9-1.1, 3Pal 0.9-1.1 (AAA)" |
| Chiral purity | L-2Nal ≤1.3%, L-4Cpa ≤0.7%, L-3Pal ≤2.0% (GC-MS) |
| Purity | ≥90% (HPLC, Area %) |

Example 2

Synthesis of Intermediate Z(4-7)OH×DCHA: Z-Ser(tBu)-4Aph(L-Hor)-D-4Aph(tBuCbm)-Leu-OH× DCHA[15]

Synthesis of Intermediate Boc(6-7)OBzl: Boc-D-4Aph(tBuCbm)-Leu-OBzl
Step 5 (Reaction Step)

Boc-D-4Aph(tBuCbm)-OH (379.45 g) is dissolved in NMP (0.76 L) and AcOEt (4.4 kg). After cooling at −4° C., IBC (150.2 g) and NMM (101.1 g) are added, and the solution stirred at −7° C. for 0.5 hour to yield Boc-D-4Aph(tBuCbm)-OAct[8].

H-Leu-OBzl×TOS (491.88 g) is dissolved in NMP (1.5 L) and AcOEt (2.7 kg) is added, followed by NMM (126.4 g). This solution is subsequently transferred to Boc-D-4Aph(tBuCbm)-OAct [8], and stirred at −10° C. for 1 hour. Then, water (0.5 L) is added.
The reaction mixture is washed at 20° C. with:
  Water at pH 8.5 (pH is adjusted while stirring with aq. NaOH)
  Water at pH 2.0 (pH is adjusted while stirring with aq. HCl)
  Water The organic phase is concentrated under reduced pressure to an oil. The oil is re-dissolved in AcOEt (0.6 kg) and re-concentrated under reduced pressure to an oil. The remaining oil is dissolved in AcOEt (0.6 kg). Heptane (15.5 L) is added while stirring at 20° C. The precipitate is isolated by filtration, and washed with heptane and subsequently dried under reduced pressure at to yield Boc-D-4Aph(tBuCbm)-Leu-OBzl[9].

Synthesis of Boc-(5-7)-OBzl: Boc-4Aph(L-Hor)-D-4Aph(tBuCbm)-Leu-OBzl
Step 6 (Reaction Step)

Boc-D-4Aph(tBuCbm)-Leu-OBzl [9] (582.7 g) from step 5 is dissolved in AcOEt (3.15 kg). MSA (481 g) is added, and stirred below 15° C. for 5 hours, and TEA (406 g) is added. DMF (0.333 kg) is added followed by TEA (101 g) and NMM (51 g) to yield H-D-4Aph(tBuCbm)-Leu-OBzl [10]. Boc-4Aph(L-Hor)-OH (462.46 g) is dissolved in DMF (2.09 kg) and AcOEt (1.44 kg). IBC (150.24 g) and NMM (111.27 g) are added, and stirred at −10° C. for 0.5 h to yield Boc-4Aph(L-Hor)-OAct[11].

H-D-4Aph(tBuCbm)-Leu-OBzl [10] is added to Boc-4Aph(L-Hor)-OAct [11] and stirred at −10° C. for 1.5 hours. Then, AcOEt (5.4 kg) and n-butanol (6.0 L) are added.
The organic phase is washed at 20° C. with:
  5% aqueous NaHCO$_3$ at about pH 8 (pH is adjusted while stirring with aq NaHCO$_3$)
  10% aqueous. NaCl at pH 2.5 (pH is adjusted while stirring with aq.H$_3$PO$_4$)

DMF (0.9 L) is added to the organic phase, which is then concentrated under reduced pressure to an oil. The solution is poured into water (14 L) while stirring. The precipitate is isolated on a filter, and washed with water. The solid is dried under reduced pressure to yield Boc-4Aph(L-Hor)-D-4Aph(tBuCbm)-Leu-OBzl[12].

Synthesis of Intermediate Z(4-7)OH×DCHA: Z-Ser(tBu)-4Aph(L-Hor)-D-4Aph(tBuCbm)-Leu-OH×DCHA (Compound of Formula Va)
Step 7 (Reaction Step)

Boc-4Aph(L-Hor)-D-4Aph(tBuCbm)-Leu-OBzl [12] (885.02 g) from step 6 is added to a mixture of MSA (961.1 g) and AcOEt (7.2 kg) and 2-butanol (2 L) is added, and the resulting mixture stirred at 0° C. for 6 hours. MSA is then neutralised with TEA (909.0 g).

5% Pd/C (88.5 g) dispersed in 2-butanol (1 L) is added and the mixture is hydrogenated under pressure at 20° C. for 3 hours. Then, the Pd/C is filtered off, and washed with 2-butanol to yield the solution containing H-4Aph(L-Hor)-D-4Aph(tBuCbm)-Leu-OH [13].

Z-Ser(tBu)-OH (413.5 g) is dissolved in MeCN (2.5 L) and the solution is cooled to −5° C. HONp (195 g) is added followed by DCC (278.5 g), and the mixture stirred at 20° C. for 24 hours. The mixture is then filtered, and washed with MeCN to yield Z-Ser(tBu)-ONp [14].

NMM (354.2 g), DMF (4.75 kg) and Z-Ser(tBu)-ONp [14] is added to the solution of H-4Aph(L-Hor)-D-4Aph(tBuCbm)-Leu-OH [13] and the mixture is left with stirring at 20° C. for 3 days.
The resulting mixture is washed with:
  10% aqueous NaCl at pH 2.5 (pH is adjusted while stirring with aqueous HCl)
  Water at acidic pH (pH 2.5) (pH is adjusted while stirring with aqueous HCl)
  7.5% aqueous NaHCO$_3$
  5% aqueous. NaCl at (pH 2.5) (pH is adjusted while stirring with aqueous HCl)
  10% aqeuous NaCl To the final organic phase DCHA (181 g) is added and the organic phase is concentrated under reduced pressure to an oil. The oil is re-dissolved in iPrOH (3.14 kg) and re-concentrated under reduced pressure to an oil. The remaining oil is re-dissolved in iPrOH (3.14 kg) and while stirring the solution is poured into AcOEt (31.5 kg). Stirring is continued at 20° C. for 1 hour until precipitation and the precipitate is then isolated by filtration, and washed with AcOEt. The solid is dried under reduced pressure at 30° C. for 30 hours to yield Z-Ser(tBu)-4Aph(L-Hor)-D-4Aph(tBuCbm)-Leu-OH×DCHA[15]. Purity of intermediate Z(4-7)OH×DCHA[15] is ≥80% (HPLC).

Step 7 Intermediate Z(4-7)OH [15]

| Quality Control | Acceptance criteria |
| --- | --- |
| Description | "White to slightly yellow powder (visual inspection)" |
| Identification (1) | "972.5 ± 0.4Da (MS)" |
| Identification (2) | "Ser 0.9-1.1, 4Aph 1.8-2.2, Leu 0.9-1.1 (AAA)" |
| Chiral purity | D-Ser ≤2.0%, D-4Aph 47-53%, D-Leu ≤0.7% (GC-MS) |
| Purity (1) | [4Aph[5] (Hydantoinacetyl)]Z(4-7)OH DCHA ≤0.5% (HPLC, Area %) |
| Purity (2) | ≥80% (HPLC, Area %) |

Example 3

Synthesis of Intermediate H(8-10)NH$_2$: H-Lys(iPr,Boc)-Pro-D-Ala-NH$_2$[21]

Synthesis of Boc(9-10)NH$_2$: Boc-Pro-D-Ala-NH$_2$
Step 8 (Reaction Step)

Boc-Pro-OH (226.02 g) is dissolved in iPrOH (1.73 kg). The reaction mixture is cooled to −5° C. IBC (143.4 g) and NMM (106.2 g) are added and the mixture is stirred at 5° C. for 0.5 hour to yield Boc-Pro-OAct[16].

H-D-Ala-NH$_2$×HCl (124.57 g) is suspended in a mixture of iPrOH (1.57 kg) and NMM (106.2 g). The suspension is added to Boc-Pro-OAct [16]. The reaction mixture is left with stirring at 10° C. for 3 hours. Then DMEDA (10.6 ml) is added. The mixture is filtered, and the filtrate is concentrated under reduced pressure to an oil. The oil is re-dissolved and re-concentrated with AcOEt (1.125 kg).

The residual oil is dissolved in a mixture of AcOEt (1.8 kg) and n-butanol (0.6 L). The organic phase is washed with:
- 15% aqueous. NaCl at pH 2.5 (pH is adjusted while stirring with aqeuous HCl)
- 15% aqueous NaCl at pH 9.5 (pH is adjusted while stirring with aqeuous NaOH)

The organic phase is concentrated under reduced pressure, re-dissolved in AcOEt (1.08 kg) and re-concentrated to an oil.

A mixture of AcOEt (0.33 kg) and heptane (0.75 L) is added at 20° C. and stirred for 16 hours. The resulting precipitate is filtered and washed with a mixture of AcOEt and heptane on the filter. The solid is then dried under reduced pressure to yield Boc-Pro-D-Ala-NH$_2$[17].

Synthesis of Intermediate H(8-10)NH$_2$: H-Lys(iPr,Boc)-Pro-D-Ala-NH$_2$ (Compound of Formula VIa)

Step 9 (Reaction Step)

Boc-Pro-D-Ala-NH$_2$ [17] (313.89 g) from Step 8 is dissolved in a mixture of MSA (528.61 g) and iPrOH (0.785 kg) and the solution is stirred at 45° C. for 1 hour. The mixture then is neutralised with TEA (607.14 g) to yield H-Pro-D-Ala-NH$_2$[18].

Z-Lys(iPr,Boc)-OH×DCHA (603.83 g) is suspended in AcOEt (1.17 kg) and washed with:
- 12% aqeuous NaHSO$_4$
- Water
- 15% aqeuous NaCl The organic phase of Z-Lys(iPr,Boc)-OH [19] from the extractions is added to H-Pro-D-Ala-NH$_2$ [18]. HOBt (183.79 g) and DCC (227.0 g) dissolved in AcOEt (0.135 kg) are added, and the mixture stirred at 20° C. for 0.5 hours. Then, water (0.2 L) is added. The mixture is filtered and washed with AcOEt. The combined filtrates are concentrated under reduced pressure to an oil. The oil is dissolved in AcOEt (0.9 kg), filtered and the solution is washed with:
- Water at pH 2.5 (pH is adjusted while stirring with aqueous HCl)
- Water at pH 9 (pH is adjusted while stirring with aqueous NaOH)
- 10% aqueous NaCl at pH 7 (pH is adjusted while stirring with aqueous HCl or aqeuous NaOH)

The organic phase is concentrated under reduced pressure to yield Z-Lys(iPro,Boc)-Pro-D-Ala-NH$_2$[20].

Z-Lys(iPro,Boc)-Pro-D-Ala-NH$_2$ [20] is dissolved in ethanol (0.04 kg) and water (0.5 L), and 5% Pd/C (50 g) is added. The slurry is acidified to pH 2.5 by addition of 6 M HCl and hydrogenated at 20° C. After completed reaction the catalyst is removed by filtration and pH is raised to pH 7.0 by addition of 32% NaOH. The ethanol is subsequently removed by evaporation under reduced pressure. n-Butanol (1 L) is added to the resulting aqueous phase and the pH is adjusted to alkaline pH 9 with aqueous NaOH and the extraction starts. This step is repeated. The combined organic phases are concentrated under reduced pressure to an oil.

The oil is dissolved in AcOBu (0.5 L), concentrated under reduced pressure at 20° C. and re-dissolved in AcOBu (0.5 L). Then, heptane (2 L) is added at 50° C. for 1 hour. The suspension is left with stirring at 0° C. for 16 hours. The precipitate is isolated by filtration and washed with heptane. Finally, the solid is dried under reduced pressure at to yield H-Lys(iPr,Boc)-Pro-D-Ala-NH$_2$[21]. Purity of intermediate H(8-10)NH$_2$[21] is ≥95% (HPLC).

Step 9 Intermediate H(8-10)NH$_2$ [21]

| Quality Control | Acceptance criteria |
|---|---|
| Description | "White to slightly yellow powder (visual inspection)" |
| Identification (1) | "456.3 ± 0.4Da (MS)" |
| Identification (2) | "Lys(iPr) 0.9-1.1, Pro 0.9-1.1, Ala 0.9-1.1 (AAA)" |
| Chiral purity | D-Lys(iPr) ≤0.3%, D-Pro ≤0.3%, L-Ala ≤0.5% (GC-MS) |
| Purity | ≥95% (HPLC, Area %) |

Example 4

Segment Condensations to Final Intermediate (Compound of Formula II)

Intermediate Z(4-10)NH$_2$: Z-Ser(tBu)-4Aph(L-Hor)-D-4Aph(tBuCbm)-Leu-Lys(iPr,Boc)-Pro-D-Ala-NH$_2$[22](Compound of Formula IVg)

Step 10 (Reaction Step)

Z-Ser(tBu)-4Aph(L-Hor)-D-4Aph(tBuCbm)-Leu-OH×DCHA [15] (1153.41 g) from Step 7 is dissolved in DMF (2.1 kg). Then, HOBt (153.2 g) is added together with AcOEt (6.9 kg) and H-Lys(iPr,Boc)-Pro-D-Ala-NH$_2$ [21] (569.5 g) from step 9. When all solids are dissolved MSA (96.1 g) is added. The solution is cooled below 5° C. and DCC (309.5 g) dissolved in AcOEt (0.810 kg) is added. The temperature is raised to 20° C. and the reaction continues for 24 hours. Conversion of Z-Ser(tBu)-4Aph(L-Hor)-D-4Aph(tBuCbm)-Leu-OH×DCHA [15] is ≥96% (HPLC). AcOEt (4.95 kg) and water (5.5 L) are added, and the mixture is stirred, and filtered.

While stirring, 7.5% NaHCO$_3$ (aq) (35 L) is added to the filtrate. The phases are separated and the organic layer is further washed with:
- 7.5% NaHCO$_3$
- Water at pH 3 (pH is adjusted while stirring with aqueous HCl)
- Water The final organic phase is concentrated under reduced pressure to an oil. The oil is re-concentrated with EtOH (0.405 kg) and subsequently with AcOEt (0.45 kg). The remaining oil is dissolved in EtOH (0.405 kg), and AcOEt (0.45 kg) and AcOBu (4.6 L) are added. The solution is added to heptane (27.6 L) at 20° C. for 1 hour. Then, the precipitate is filtered, and washed with heptane. The solid is dried under reduced pressure at maximum to yield Z-Ser(tBu)-4Aph(L-Hor)-D-4Aph(tBuCbm)-Leu-Lys(iPr,Boc)-Pro-D-Ala-NH$_2$[22]. Purity of Z-Ser(tBu)-4Aph(L-Hor)-D-4Aph(tBuCbm)-Leu-Lys(iPr,Boc)-Pro-D-Ala-NH$_2$ [22] is ≥70% (HPLC).

Final Intermediate Ac(1-10)NH$_2$: Ac-D-2Nal-D-4Cpa-D-3Pal-Ser(tBu)-4Aph(L-Hor)-D-4Aph(tBuCbm)-Leu-Lys(iPr,Boc)-Pro-D-Ala-NH$_2$[24]

Step 11 (Reaction Step)

Z-Ser(tBu)-4Aph(L-Hor)-D-4Aph(tBuCbm)-Leu-Lys(iPr,Boc)-Pro-D-Ala-NH$_2$ [22] (1409.67 g) from Step 10 is added to a mixture of EtOH (10.98 kg) and water (3.2 L) and stirred until the solution is homogenous. 5% Pd/C (211 g) is added. The mixture is hydrogenated at 20° C. with pH-control at pH 2.5, with aqueous HCl.

The catalyst is removed by filtration and the pH is adjusted to pH 3.8, with aqueous NaOH. The filtrate is concentrated under reduced pressure to an oil. EtOH (4.7 kg) is added to the oil and re-concentrated. Then, AcOEt (5.4 kg) is added to the oil and re-concentrated and this process is repeated again to yield H-Ser(tBu)-4Aph(L-Hor)-D-4Aph(tBuCbm)-Leu-Lys(iPr,Boc)-Pro-D-Ala-NH$_2$[23].

H-Ser(tBu)-4Aph(L-Hor)-D-4Aph(tBuCbm)-Leu-Lys(iPr,Boc)-Pro-D-Ala-NH$_2$ [23] is dispersed in AcOEt (1.125 kg), then HOBt (153.16 g) is added and the mixture is cooled to 0° C. Ac-D-2Nal-D-4Cpa-D-3Pal-ONa [7] (609.05 g) from Step 4 is dissolved in DMSO (2.5 L), this solution is mixed with the slurry containing H-Ser(tBu)-4Aph(L-Hor)-D-4Aph(tBuCbm)-Leu-Lys(iPr,Boc)-Pro-D-Ala-NH$_2$ [23] and DCC (309.5 g) dissolved in AcOEt (0.45 kg) is added. The mixture is stirred at 5° C. for 24 hours. Conversion of [23] is ≥96% (HPLC).

Water (150 mL) and DMSO (0.5 L) are added and the stirring is continued at 20° C. for more than 3 hours. The precipitate is filtered, and washed with a mixture of AcOEt and DMSO. The filtrates are combined, and n-butanol (17 L) is added. The organic solution is washed with:

Water at pH 2.5 (pH is adjusted while stirring with aqueous HCl)

7% NaHCO$_3$ (aq)

10% aqueous NaCl (pH in the mixture is neutralised to pH 7.0, if necessary, while stirring with aqueous HCl)

DMF (4.75 kg) is added and the organic phase is concentrated under reduced pressure to an oil. The oil is slowly added to water (50 L) at 20° C. for 1 hour under vigorous stirring. The precipitate is isolated on a filter, and washed twice with water. The solid is subsequently dried under reduced pressure to yield AC-D-2Nal-D-4Cpa-D-3Pal-Ser(tBu)-4Aph(L-Hor)-D-4Aph(tBuCbm)-Leu-Lys(iPr,Boc)-Pro-D-Ala-NH$_2$[24][Final intermediate]. Purity of [24] is ≥70% (HPLC)

Example 5

Deprotection of Final Intermediate Ac(1-10)NH$_2$ to Crude Degarelix[25]

Step 12 (Reaction Step)

Ac-D-2Nal-D-4Cpa-D-3 Pal-Ser(tBu)-4Aph(L-Hor)-D-4Aph(tBuCbm)-Leu-Lys(iPr,Boc)-Pro-D-Ala-NH$_2$ [24] (Compound of formula IIb)(1844.59 g) from step 11 is dissolved in TFA (28.3 kg) at 20° C. The solution is stirred at 20° C. (removal of 3 protection groups) for 24 hours. Conversion of [24] is ≥99% (HPLC).

The reaction mixture is then mixed with a cold solution (below 10° C.) of water (74 L), AcONH$_4$ (19.1 kg), AcOH (18.4 L) and EtOH (14.52 kg). During mixing of the two solutions the temperature is kept below 25° C. The pH of the final solution is adjusted to pH 3 with TFA or AcONH$_4$, if necessary, to yield the solution of Ac-D-2Nal-D-4Cpa-D-3Pal-Ser-4Aph(L-Hor)-D-4Aph(Cbm)-Leu-Lys(iPr)-Pro-D-Ala-NH$_2$[25][Crude Degarelix].

Step 13 (Purification and Lyophilisation)

The solution of crude degarelix is pumped through a reversed phase column. Degarelix is eluted from the column with a gradient of EtOH/0.12% TFA in water. Fractions with a purity ≥95% are repurified on a reversed phase column using a gradient of EtOH/1% AcOH in water. Fractions of high purity are lyophilised.

The invention claimed is:

1. A process for preparing Degarelix having the formula Ac-AA$_1$-AA$_{10}$-NH$_2$ or a pharmaceutically acceptable salt or solvate thereof, wherein AA$_1$ is D-2Nal, AA$_2$ is D-4Cpa, AA$_3$ is D-3Pal, AA$_4$ is Ser, AA$_5$ is 4Aph(L-Hor), AA$_6$ is D-Aph(Cbm), AA$_7$ is Leu, AA$_8$ is Lys(iPr), AA$_9$ is Pro and AA$_{10}$ is D-Ala, comprising:

treating a Degarelix precursor according to formula II ((P$_1$)AA$_1$-AA$_2$-AA$_3$-AA$_4$(P$_4$)-AA$_5$-AA$_6$(P$_6$)-AA$_7$-AA$_8$(P$_8$)-AA$_9$-AA$_{10}$-NH$_2$), or a salt or solvate thereof, with a cleaving agent, wherein formula II is as follows:

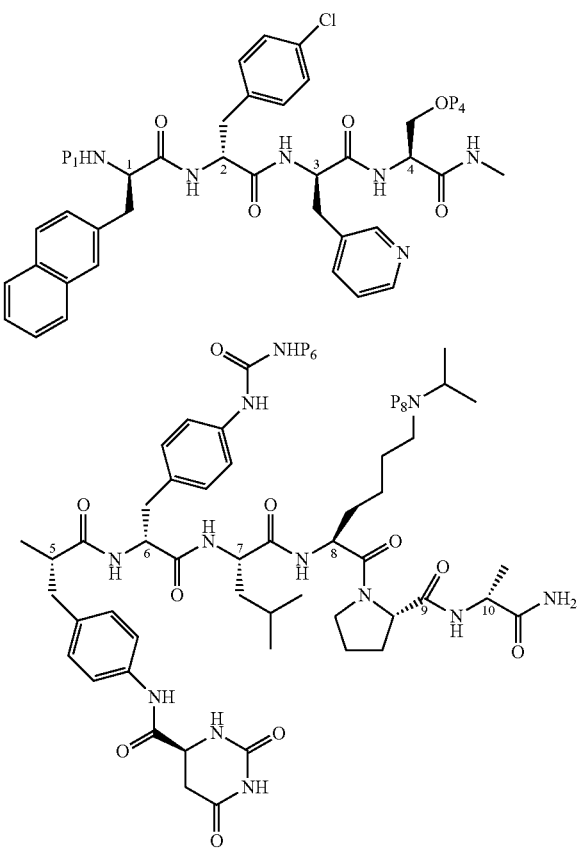

wherein

P$_1$ is an amino protecting group;

P$_4$ is hydrogen or a hydroxyl protecting group;

P$_6$ is hydrogen or an amino protecting group;

P$_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl](Ddz), 2,2,2-trichloroethyloxycarbonyl (Troc), biphenylylisopropyloxycarbonyl (Bpoc), and o-nitrobenzyloxycarbonyl; and wherein the process is a liquid-phase process, or a process for preparing Degarelix having the formula Ac-AA$_1$-AA$_{10}$-NH$_2$ or a pharmaceutically acceptable salt or solvate thereof, wherein AA$_1$ is D-2Nal, AA$_2$ is D-4Cpa, AA$_3$ is D-3Pal, AA$_4$ is Ser, AA$_5$ is 4Aph(L-Hor), AA$_6$ is D-Aph(Cbm), AA$_7$ is Leu, AA$_8$ is Lys(iPr), AA$_9$ is Pro and AA$_{10}$ is D-Ala, comprising:

treating a Degarelix precursor according to formula II
((P₁)AA₁-AA₂-AA₃-AA₄(P₄)-AA₅-AA₆(P₆)-AA₇-AA₈(P₈)-AA₉-AA₁₀-NH₂), or a salt or solvate thereof, with a cleaving agent, wherein formula II is as follows:

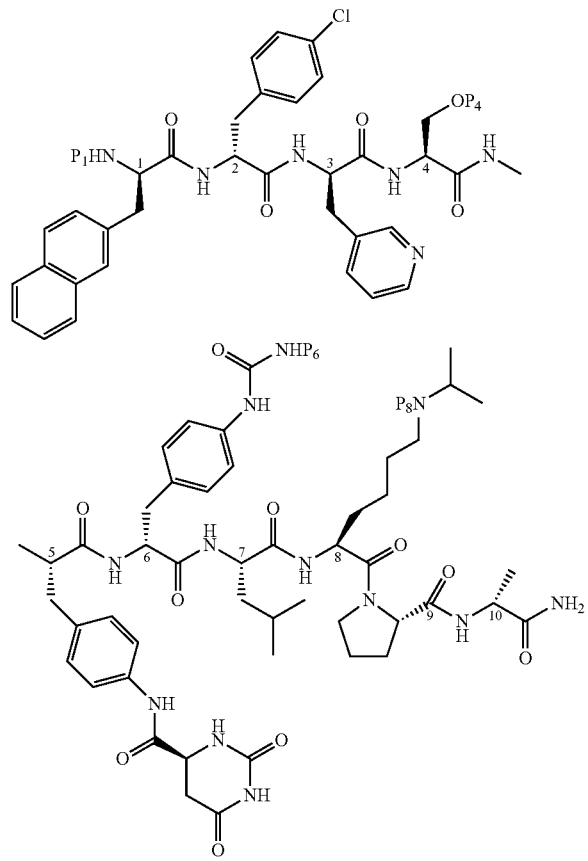

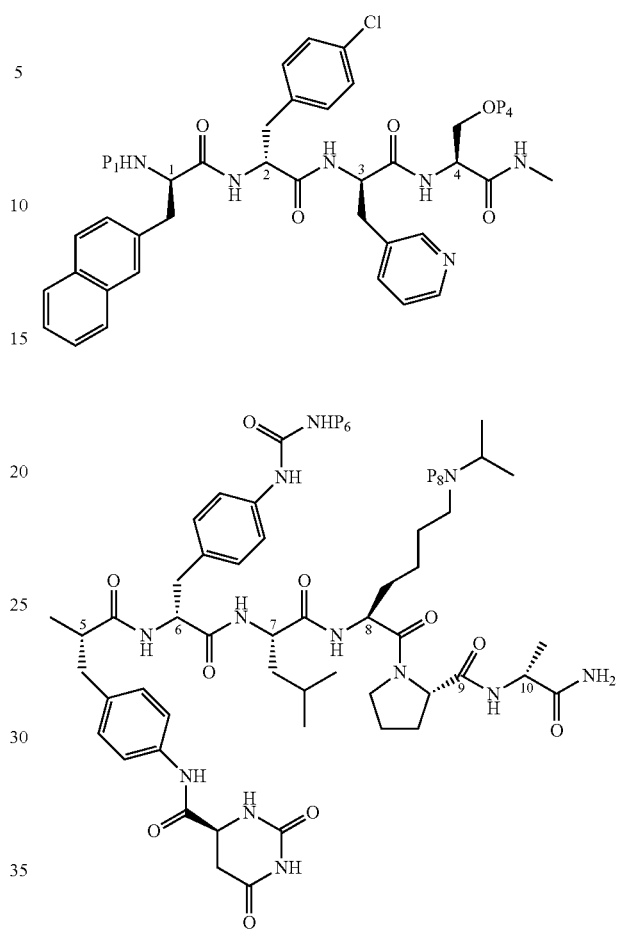

wherein

P₁ is an amino protecting group;

P₄ is hydrogen or a hydroxyl protecting group;

P₆ is hydrogen or an amino protecting group chosen from C₅-C₆ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C₁-C₆)alkylsilyl, 2-methoxyethoxymethyl (MEM), 4-dimethylcarbamoylbenzyl, 9-fluorenylmethyl ethers, and O-phenoxyacetyl ethers;

P₈ is an amino protecting group; and wherein the process is a liquid-phase process, or a process for preparing Degarelix having the formula Ac-AA₁-AA₁₀-NH₂ or a pharmaceutically acceptable salt or solvate thereof, wherein AA₁ is D-2Nal, AA₂ is D-4Cpa, AA₃ is D-3Pal, AA₄ is Ser, AA₅ is 4Aph(L-Hor), AA₆ is D-Aph(Cbm), AA₇ is Leu, AA₈ is Lys (iPr), AA₉ is Pro and AA₁₀ is D-Ala, comprising:

treating a Degarelix precursor according to formula II ((P₁)AA₁-AA₂-AA₃-AA₄(P₄)-AA₅-AA₆(P₆)-AA₇-AA₈(P₈)-AA₉-AA₁₀-NH₂), or a salt or solvate thereof, with a cleaving agent, wherein formula II is as follows:

wherein

P₁ is an amino protecting group;

P₄ is hydrogen or is a hydroxyl protecting group chosen from C₅-C₆ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C₁-C₆)alkylsilyl, 2-methoxyethoxymethyl (MEM), 4-dimethylcarbamoylbenzyl, 9-fluorenylmethyl ethers, and O-phenoxyacetyl ethers;

P₆ is hydrogen or an amino protecting group;

P₈ is an amino protecting group; and wherein the process is a liquid-phase process, or a process for preparing Degarelix having the formula Ac-AA₁-AA₁₀-NH₂ or a pharmaceutically acceptable salt or solvate thereof, wherein AA₁ is D-2Nal, AA₂ is D-4Cpa, AA₃ is D-3Pal, AA₄ is Ser, AA₅ is 4Aph(L-Hor), AA₆ is D-Aph(Cbm), AA₇ is Leu, AA₈ is Lys (iPr), AA₉ is Pro and AA₁₀ is D-Ala, comprising:

treating a Degarelix precursor according to formula II ((P₁)AA₁-AA₂-AA₃-AA₄(P₄)-AA₅-AA₆(P₆)-AA₇-AA₈(P₈)-AA₉-AA₁₀-NH₂), or a salt or solvate thereof, with a cleaving agent, wherein formula II is as follows:

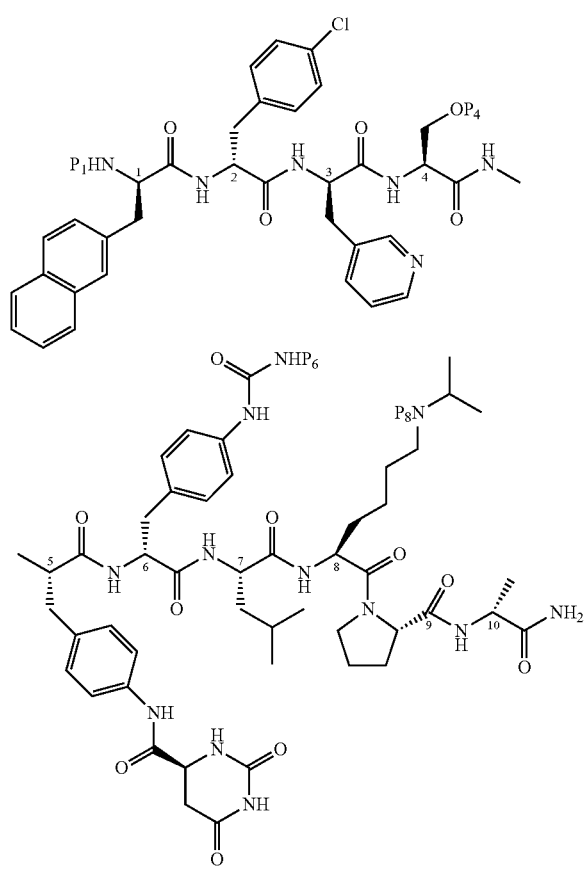

wherein
  P$_1$ is an amino protecting group;
  P$_4$ is hydrogen or is a hydroxyl protecting group chosen from C$_5$-C$_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C$_1$-C$_6$)alkylsilyl, 2-methoxyethoxymethyl (MEM), 4-dimethylcarbamoylbenzyl, 9-fluorenylmethyl ethers, and O-phenoxyacetyl ethers;
  P$_6$ is hydrogen or an amino protecting group chosen from C$_5$-C$_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C$_1$-C$_6$)alkylsilyl, 2-methoxyethoxymethyl (MEM), 4-dimethylcarbamoylbenzyl, 9-fluorenylmethyl ethers, and O-phenoxyacetyl ethers;
  P$_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl; and
wherein the process is a liquid-phase process.

2. A process for the manufacture of a decapeptide represented by formula (II)

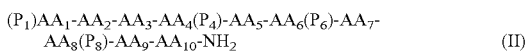

wherein AA$_1$ is D-2Nal, AA$_2$ is D-4Cpa, AA$_3$ is D-3Pal, AA$_4$ is Ser, AA$_5$ is 4Aph(L-Hor), AA$_6$ is D-Aph(Cbm), AA$_7$ is Leu, AA$_8$ is Lys(iPr), AA$_9$ is Pro, and AA$_{10}$ is D-Ala;
  P$_1$ is an amino protecting group or acetyl;
  P$_4$ is hydrogen or is a hydroxyl protecting group chosen from C$_5$-C$_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C$_1$-C$_6$)alkylsilyl, 2-methoxyethoxymethyl (MEM), 4-dimethylcarbamoylbenzyl, 9-fluorenylmethyl ethers, and O-phenoxyacetyl ethers;
  P$_6$ is hydrogen or an amino protecting group; and
  P$_8$ is an amino protecting group, or a pharmaceutically acceptable salt or solvate thereof, comprising the step of coupling a first polypeptide represented by formula (III):

or a salt thereof, with a second polypeptide represented by formula (IV):

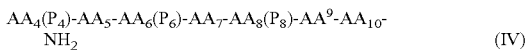

or a salt thereof, in a liquid reagent medium in the presence of a peptide coupling reagent,
wherein the process is a liquid-phase process,
or
a process for the manufacture of a decapeptide represented by formula (II)

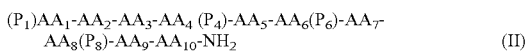

wherein AA$_1$ is D-2Nal, AA$_2$ is D-4Cpa, AA$_3$ is D-3Pal, AA$_4$ is Ser, AA$_5$ is 4Aph(L-Hor), AA$_6$ is D-Aph(Cbm), AA$_7$ is Leu, AA$_8$ is Lys(iPr), AA$_9$ is Pro, and AA$_{10}$ is D-Ala;
  P$_1$ is an amino protecting group or acetyl;
  P$_4$ is hydrogen or a hydroxyl protecting group;
  P$_6$ is hydrogen or an amino protecting group chosen from C$_5$-C$_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri(C$_1$-C$_6$)alkylsilyl, 2-methoxyethoxymethyl (MEM), 4-dimethylcarbamoylbenzyl, 9-fluorenylmethyl ethers, and O-phenoxyacetyl ethers; and
  P$_8$ is an amino protecting group, or a pharmaceutically acceptable salt or solvate thereof, comprising the step of
coupling a first polypeptide represented by formula (III):

or a salt thereof, with a second polypeptide represented by formula (IV):

$$AA_4(P_4)\text{-}AA_5\text{-}AA_6(P_6)\text{-}AA_7\text{-}AA_8(P_8)\text{-}AA_9\text{-}AA_{10}\text{-}NH_2 \quad (IV)$$

or a salt thereof, in a liquid reagent medium in the presence of a peptide coupling reagent,
wherein the process is a liquid-phase process,
or
a process for the manufacture of a decapeptide represented by formula (II)

$$(P_1)AA_1\text{-}AA_2\text{-}AA_3\text{-}AA_4(P_4)\text{-}AA_5\text{-}AA_6(P_6)\text{-}AA_7\text{-}AA_8(P_8)\text{-}AA_9\text{-}AA_{10}\text{-}NH_2 \quad (II)$$

wherein $AA_1$ is D-2Nal, $AA_2$ is D-4Cpa, $AA_3$ is D-3Pal, $AA_4$ is Ser, $AA_5$ is 4Aph(L-Hor), $AA_6$ is D-Aph(Cbm), $AA_7$ is Leu, $AA_8$ is Lys(iPr), $AA_9$ is Pro, and $AA_{10}$ is D-Ala;
$P_1$ is an amino protecting group or acetyl;
$P_4$ is hydrogen or a hydroxyl protecting group;
$P_6$ is hydrogen or an amino protecting group; and
$P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl, or a pharmaceutically acceptable salt or solvate thereof, comprising the step of
coupling a first polypeptide represented by formula (III):

$$(P_1)AA_1\text{-}AA_2\text{-}AA_3 \quad (III)$$

or a salt thereof, with a second polypeptide represented by formula (IV):

$$AA_4(P_4)\text{-}AA_5\text{-}AA_6(P_6)\text{-}AA_7\text{-}AA_8(P_8)\text{-}AA_9\text{-}AA_{10}\text{-}NH_2 \quad (IV)$$

or a salt thereof, in a liquid reagent medium in the presence of a peptide coupling reagent,
wherein the process is a liquid-phase process,
or
a process for the manufacture of a decapeptide represented by formula (II)

$$(P_1)AA_1\text{-}AA_2\text{-}AA_3\text{-}AA_4(P_4)\text{-}AA_5\text{-}AA_6(P_6)\text{-}AA_7\text{-}AA_8(P_8)\text{-}AA_9\text{-}AA_{10}\text{-}NH_2 \quad (II)$$

wherein $AA_1$ is D-2Nal, $AA_2$ is D-4Cpa, $AA_3$ is D-3Pal, $AA_4$ is Ser, $AA_5$ is 4Aph(L-Hor), $AA_6$ is D-Aph(Cbm), $AA_7$ is Leu, $AA_8$ is Lys(iPr), $AA_9$ is Pro, and $AA_{10}$ is D-Ala;
$P_1$ is an amino protecting group or acetyl;
$P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers;
$P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers; and
$P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chloro-benzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl, or a pharmaceutically acceptable salt or solvate thereof, comprising the step of
coupling a first polypeptide represented by formula (III):

$$(P_1)AA_1\text{-}AA_2\text{-}AA_3 \quad (III)$$

or a salt thereof, with a second polypeptide represented by formula (IV):

$$AA_4(P_4)\text{-}AA_5\text{-}AA_6(P_6)\text{-}AA_7\text{-}AA_8(P_8)\text{-}AA_9\text{-}AA_{10}\text{-}NH_2 \quad (IV)$$

or a salt thereof, in a liquid reagent medium in the presence of a peptide coupling reagent,
wherein the process is a liquid-phase process.

3. A process for preparing a polypeptide represented by formula (IV):

$$(P_4)AA_4\text{-}AA_5\text{-}AA_6(P_6)\text{-}AA_7\text{-}AA_8(P_8)\text{-}AA_9\text{-}AA_{10}\text{-}NH_2 \quad (IV)$$

wherein
$P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers;
$P_6$ is hydrogen or an amino protecting group; and
$P_8$ is an amino protecting group, comprising:
coupling a polypeptide represented by formulae (V), or a salt or solvate thereof, with a polypeptide represented by formula (VI), or a salt or solvate thereof, $$(P_N)AA_4(P_4)\text{-}AA_5\text{-}AA_6(P_6)\text{-}AA_7 \quad (V)$$

$$AA_8(P_8)\text{-}AA_9\text{-}AA_{10}\text{-}NH_2 \quad (VI)$$

and then removing the deprotecting group $P_N$, wherein $AA_4$ is Ser, $AA_5$ is 4Aph(L-Hor), $AA_6$ is D-Aph(Cbm), AA₇ is Leu, AA₈ is Lys(iPr), AA₉ is Pro and AA₁₀ is D-Ala, and $P_N$ is a protecting group that can be removed by hydrogenation, wherein the process is a liquid-phase process, or a process for preparing a polypeptide represented by formula (IV):

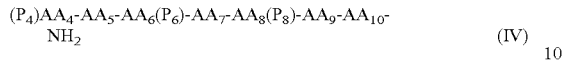

(P₄)AA₄-AA₅-AA₆(P₆)-AA₇-AA₈(P₈)-AA₉-AA₁₀-NH₂     (IV)

wherein $P_4$ is hydrogen or a hydroxyl protecting group;

$P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers; and $P_8$ is an amino protecting group, comprising:

coupling a polypeptide represented by formulae (V), or a salt or solvate thereof, with a polypeptide represented by formula (VI), or a salt or solvate thereof,

($P_N$)AA₄(P₄)-AA₅-AA₆(P₆)-AA₇     (V)

AA₈(P₈)-AA₉-AA₁₀-NH₂     (VI)

and then removing the deprotecting group $P_N$, wherein AA₄ is Ser, AA₅ is 4Aph(L-Hor), AA₆ is D-Aph(Cbm), AA₇ is Leu, AA₈ is Lys(iPr), AA₉ is Pro and AA₁₀ is D-Ala, and $P_N$ is a protecting group that can be removed by hydrogenation, wherein the process is a liquid-phase process, or a process for preparing a polypeptide represented by formula (IV):

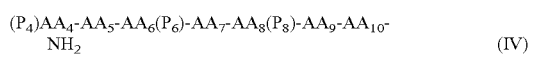

(P₄)AA₄-AA₅-AA₆(P₆)-AA₇-AA₈(P₈)-AA₉-AA₁₀-NH₂     (IV)

wherein $P_4$ is hydrogen or a hydroxyl protecting group;

$P_6$ is hydrogen or an amino protecting group; and $P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbonyl, comprising:

coupling a polypeptide represented by formulae (V), or a salt or solvate thereof, with a polypeptide represented by formula (VI), or a salt or solvate thereof,

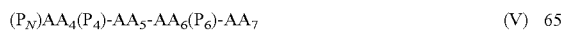

($P_N$)AA₄(P₄)-AA₅-AA₆(P₆)-AA₇     (V)

AA₈(P₈)-AA₉-AA₁₀-NH₂     (VI)

and then removing the deprotecting group $P_N$, wherein AA₄ is Ser, AA₅ is 4Aph(L-Hor), AA₆ is D-Aph(Cbm), AA₇ is Leu, AA₈ is Lys(iPr), AA₉ is Pro and AA₁₀ is D-Ala, and $P_N$ is a protecting group that can be removed by hydrogenation, wherein the process is a liquid-phase process, or a process for preparing a polypeptide represented by formula (IV):

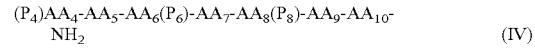

(P₄)AA₄-AA₅-AA₆(P₆)-AA₇-AA₈(P₈)-AA₉-AA₁₀-NH₂     (IV)

wherein $P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers;

$P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers; and $P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbony, comprising:

coupling a polypeptide represented by formulae (V), or a salt or solvate thereof, with a polypeptide represented by formula (VI), or a salt or solvate thereof,

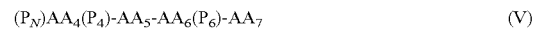

($P_N$)AA₄(P₄)-AA₅-AA₆(P₆)-AA₇     (V)

AA₈(P₈)-AA₉-AA₁₀-NH₂     (VI)

and then removing the deprotecting group $P_N$, wherein AA₄ is Ser, AA₅ is 4Aph(L-Hor), AA₆ is D-Aph(Cbm), AA₇ is Leu, AA₈ is Lys(iPr), AA₉ is Pro and AA₁₀ is D-Ala, and $P_N$ is a protecting group that can be removed by hydrogenation, wherein the process is a liquid-phase process.

4. A process for producing a compound of ($P_N$)AA₄(P₄)-AA₅-AA₆(P₆)-AA₇, wherein AA₄ is Ser, AA₅ is 4Aph(L-Hor), AA₆ is D-Aph(Cbm), AA₇ is Leu, $P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers, $P_6$ is chosen from hydrogen and an amino protecting group, and $P_N$ is a protecting group that can be removed by hydrogenation, comprising the following steps:

(a) providing ($P_{N2}$)$AA_5$-$AA_6$($P_6$)-$AA_7$($P_c$), wherein ($P_{N2}$) is an N-terminal amino protecting group or hydrogen, and ($P_c$) is a C-terminal carboxyl protecting group that can be cleaved by hydrogenation;

(b) removing the amino protecting group ($P_{N2}$), if present;

(c) hydrogenating H-$AA_5$-$AA_6$($P_6$)-$AA_7$($P_c$) to obtain H-$AA_5$-$AA_6$($P_6$)-$AA_7$; and (d) reacting H-$AA_5$-$AA_6$($P_6$)-$AA_7$ with an activated ester of ($P_N$)$AA_4$($P_4$) to provide ($P_N$)$AA_4$($P_4$)-$AA_5$-$AA_6$($P_6$)-$AA_7$, wherein ($P_4$) is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers or hydrogen, and $P_N$ is a protecting group that can be eliminated by hydrogenation, wherein the process is a liquid-phase process, or a process for producing a compound of ($P_N$)$AA_4$($P_4$)-$AA_5$-$AA_6$($P_6$)-$AA_7$, wherein $AA_4$ is Ser, $AA_5$ is 4Aph(L-Hor), $AA_6$ is D-Aph (Cbm), $AA_7$ is Leu, $P_4$ is chosen from hydrogen and a hydroxyl protecting group, $P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers, and $P_N$ is a protecting group that can be removed by hydrogenation, comprising the following steps:

(a) providing ($P_{N2}$)$AA_5$-$AA_6$($P_6$)-$AA_7$($P_c$), wherein ($P_{N2}$) is an N-terminal amino protecting group or hydrogen, and ($P_c$) is a C-terminal carboxyl protecting group that can be cleaved by hydrogenation;

(b) removing the amino protecting group ($P_{N2}$), if present;

(c) hydrogenating H-$AA_5$-$AA_6$($P_6$)-$AA_7$($P_c$) to obtain H-$AA_5$-$AA_6$($P_6$)-$AA_7$; and (d) reacting H-$AA_5$-$AA_6$($P_6$)-$AA_7$ with an activated ester of ($P_N$)$AA_4$($P_4$) to provide ($P_N$)$AA_4$($P_4$)-$AA_5$-$AA_6$($P_6$)-$AA_7$, wherein ($P_4$) is a hydroxyl protecting group or hydrogen, and $P_N$ is a protecting group that can be eliminated by hydrogenation, wherein the process is a liquid-phase process, or a process for producing a compound of ($P_N$)$AA_4$($P_4$)-$AA_5$-$AA_6$($P_6$)-$AA_7$, wherein $AA_4$ is Ser, $AA_5$ is 4Aph(L-Hor), $AA_6$ is D-Aph (Cbm), $AA_7$ is Leu, $P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers, $P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers, and $P_N$ is a protecting group that can be removed by hydrogenation, comprising the following steps:

(a) providing ($P_{N2}$)$AA_5$-$AA_6$($P_6$)-$AA_7$($P_c$), wherein ($P_{N2}$) is an N-terminal amino protecting group or hydrogen, and ($P_c$) is a C-terminal carboxyl protecting group that can be cleaved by hydrogenation;

(b) removing the amino protecting group ($P_{N2}$), if present;

(c) hydrogenating H-$AA_5$-$AA_6$($P_6$)-$AA_7$($P_c$) to obtain H-$AA_5$-$AA_6$($P_6$)-$AA_7$; and (d) reacting H-$AA_5$-$AA_6$($P_6$)-$AA_7$ with an activated ester of ($P_N$)$AA_4$($P_4$) to provide ($P_N$)$AA_4$($P_4$)-$AA_5$-$AA_6$($P_6$)-$AA_7$, wherein ($P_4$) is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers or hydrogen, and $P_N$ is a protecting group that can be eliminated by hydrogenation, wherein the process is a liquid-phase process.

5. Polypeptide compounds consisting of the following formulae:

$$AA_4(P_4)\text{-}AA_5\text{-}AA_6(P_6)\text{-}AA_7\text{-}AA_8(P_8)\text{-}AA_9\text{-}AA_{10}\text{-}NH_2,$$

$$(P_N)AA_4(P_4)\text{-}AA_5\text{-}AA_6(P_6)\text{-}AA_7\text{-}AA_8(P_8)\text{-}AA_9\text{-}AA_{10}\text{-}NH_2,$$

$$(P_N)AA_4(P_4)\text{-}AA_5\text{-}AA_6(P_6)\text{-}AA_7, \text{ or salts or solvates,}$$

wherein $AA_4$ is Ser, $AA_5$ is 4Aph(L-Hor), $AA_6$ is D-Aph (Cbm), $AA_7$ is Leu, $AA_8$ is Lys(iPr), AA9 is Pro, $AA_{10}$ is D-Ala;

$P_4$ is hydrogen or is a hydroxyl protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers;

$P_6$ is hydrogen or an amino protecting groups; and $P_8$ is an amino protecting group, and $P_N$ is a protecting group, or polypeptide compounds represented by the following formulae:

$$AA_4(P_4)\text{-}AA_5\text{-}AA_6(P_6)\text{-}AA_7\text{-}AA_8(P_8)\text{-}AA_9\text{-}AA_{10}\text{-}NH_2,$$

$$(P_N)AA_4(P_4)\text{-}AA_5\text{-}AA_6(P_6)\text{-}AA_7\text{-}AA_8(P_8)\text{-}AA_9\text{-}AA_{10}\text{-}NH_2,$$

$$(P_N)AA_4(P_4)\text{-}AA_5\text{-}AA_6(P_6)\text{-}AA_7, \text{ or salts or solvates,}$$

wherein $AA_4$ is Ser, $AA_5$ is 4Aph(L-Hor), $AA_6$ is D-Aph (Cbm), $AA_7$ is Leu, $AA_8$ is Lys(iPr), $AA_9$ is Pro, $AA_{10}$ is D-Ala;

$P_4$ is hydrogen or a hydroxyl protecting group;

$P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers; and $P_8$ is an amino protecting group, and $P_N$ is a protecting group, or polypeptide compounds represented by the following formulae:

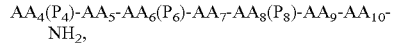

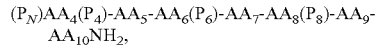

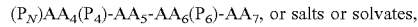

wherein $AA_4$ is Ser, $AA_5$ is 4Aph(L-Hor), $AA_6$ is D-Aph(Cbm), $AA_7$ is Leu, $AA_8$ is Lys(iPr), AA9 is Pro, $AA_{1o}$ is D-Ala;

$P_4$ is hydrogen or a hydroxyl protecting group;

$P_6$ is hydrogen or an amino protecting groups; and $P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbony, and $P_N$ is a protecting group, or polypeptide compounds represented by the following formulae:

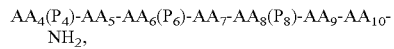

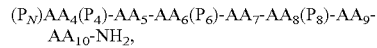

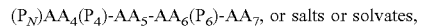

wherein $AA_4$ is Ser, $AA_5$ is 4Aph(L-Hor), $AA_6$ is D-Aph(Cbm), $AA_7$ is Leu, $AA_8$ is Lys(iPr), AA9 is Pro, $AA_{10}$ is D-Ala;

$P_4$ is hydrogen or is a hydroxyl group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers;

$P_6$ is hydrogen or an amino protecting group chosen from $C_5$-$C_6$ alkyl, acetyl (Ac), trityl, benzyl, p-methoxybenzyl, p-nitrobenzyl, p-chlorobenzyl, o-chlorobenzyl, 2,6-dichlorobenzyl, tetrahydropyranyl, tri($C_1$-$C_6$)alkylsilyl, 2-methoxyethoxymethyl (MEM), 4-dimethylcarbamoylbenzyl, 9-fluorenylmethyl ethers, and O-phenoxyacetyl ethers; and $P_8$ is an amino protecting group chosen from 9-fluorenylmethyloxycarbonyl (Fmoc), benzyloxycarbonyl (Cbz or Z), 2-bromo-benzyloxycarbonyl (2-Br—Z), 2-chlorobenzyloxycarbonyl (2-Cl—Z), p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, t-amyloxycarbonyl, isopropyloxycarbonyl, 2-(p-biphenylyl)-isopropyloxycarbonyl, cyclopentyloxycarbonyl, adamantyloxycarbonyl, cyclohexyloxycarbonyl, allyloxycarbonyl (Alloc) acetyl (Ac), benzoyl (Bz), trifluoroacetyl (Tfa), toluenesulfonyl (Tos), benzyl (Bn), triphenylmethyl (Trt), o-nitrophenyl-sulfenyl (Nps), t-butyl-dimethylsilyloxycarbonyl, [2-(3,5-dimethoxyphenyl)-propyl-2-oxycarbonyl] (Ddz), 2,2,2-trichloroethyloxycarbonyl (Troc), biphenylylisopropyloxycarbonyl (Bpoc), and o-nitrobenzyloxycarbony, and $P_N$ is a protecting group.

* * * * *

UNITED STATES PATENT AND TRADEMARK OFFICE
CERTIFICATE OF CORRECTION

PATENT NO. : 9,822,146 B2
APPLICATION NO. : 14/747218
DATED : November 21, 2017
INVENTOR(S) : Jon Holbech Rasmusse et al.

It is certified that error appears in the above-identified patent and that said Letters Patent is hereby corrected as shown below:

In the Claims

Claim 2, Column 28, Line 36, "$AA^9$" should read --$AA_9$--.

Claim 3, Column 32, Line 3, "$AA_5$ is Lys(iPr)" should read --$AA_8$ is Lys(iPr)--.

Claim 4, Column 33, Lines 8, 43, 45, 48; Column 34, Lines 10, 12, 15, "$(P_c)$" should read --$(P_C)$--.

Claim 5, Column 34, Line 39; Column 35, Line 19; Column 36, Line 8, "AA9" should read --$AA_9$--.

Claim 5, Column 35, Line 19, "$AA_{1o}$" should read --$AA_{10}$--.

Signed and Sealed this
Twenty-ninth Day of May, 2018

Andrei Iancu
*Director of the United States Patent and Trademark Office*